(12) United States Patent
Engelen et al.

(10) Patent No.: US 9,057,073 B2
(45) Date of Patent: Jun. 16, 2015

(54) DIFFERENTIAL EXPRESSION OF SUBGENOME SPECIFIC ALLELES IN COTTON AND USES THEREOF

(75) Inventors: Steven Engelen, Lokeren (BE); Antonio Arioli, Lubbock, TX (US)

(73) Assignee: BAYER CROPSCIENCE N.V., Diegem (BE)

( * ) Notice: Subject to any disclaimer, the term of this patent is extended or adjusted under 35 U.S.C. 154(b) by 1059 days.

(21) Appl. No.: 12/522,806

(22) PCT Filed: Jan. 7, 2008

(86) PCT No.: PCT/EP2008/000161
§ 371 (c)(1),
(2), (4) Date: Jan. 12, 2010

(87) PCT Pub. No.: WO2008/083969
PCT Pub. Date: Jul. 17, 2008

(65) Prior Publication Data
US 2010/0115659 A1 May 6, 2010

Related U.S. Application Data

(60) Provisional application No. 60/884,564, filed on Jan. 11, 2007.

(30) Foreign Application Priority Data

Jan. 11, 2007 (EP) .................................... 07000550

(51) Int. Cl.
*C12N 15/82* (2006.01)
(52) U.S. Cl.
CPC .................................. *C12N 15/8234* (2013.01)
(58) Field of Classification Search
None
See application file for complete search history.

(56) References Cited

U.S. PATENT DOCUMENTS

| 5,004,863 | A | 4/1991 | Umbeck |
| 5,792,933 | A | 8/1998 | Ma |
| 6,166,294 | A | 12/2000 | Kasukabe et al. |
| 6,259,003 | B1 | 7/2001 | Fujisawa et al. |
| 6,483,013 | B1 | 11/2002 | Reynaerts et al. |

FOREIGN PATENT DOCUMENTS

| EP | 1 339 859 | 7/2008 |
| WO | WO 92/15675 | 9/1992 |
| WO | WO 98/30698 | 7/1998 |
| WO | WO 99/53050 | 10/1999 |
| WO | WO 99/53053 | 10/1999 |
| WO | WO 00/71733 | 11/2000 |
| WO | WO 02/10377 | 2/2002 |
| WO | WO 02/10413 | 2/2002 |
| WO | WO 02/45485 | 6/2002 |
| WO | WO 02/059294 | 8/2002 |
| WO | WO 03/076619 | 9/2003 |
| WO | WO 2004/018620 | 3/2004 |
| WO | WO 2005/017157 | 2/2005 |
| WO | WO 2005/047505 | 5/2005 |
| WO | WO 2006/044322 | 4/2006 |
| WO | WO 2006/136351 | 12/2006 |

OTHER PUBLICATIONS

Kim et al, Plant Mol Biol 24: 105-117, 1994.*
Amor et al., "A Membrane-Associated Form of Sucrose Synthase and its Potential Role in Synthesis of Cellulose and Callose in Plants", Proceedings of the National Academy of Sciences of the United States of America, vol. 92, pp. 9353-9357, Sep. 1995.
Arioli et al., "Molecular Analysis of Cellulose Biosynthesis in Arabidopsis", Science, vol. 279, pp. 717-720, Jan. 1998.
Delmer, "Cellulose Biosynthesis: Exciting Times for a Difficult Field of Study", Annual Review of Plant Physiology and Plant Molecular Biology, vol. 50, pp. 245 276 (1999).
Feng and Brown, "A Novel Cotton Ovule Culture: Induction, Growth, and Characterization of Submerged Cotton Fibers (Gossypium Hirsutum L.)", In Vitro Cellular & Developmental Biology, vol. 36, No. 4, pp. 293-299, Jul.-Aug. 2000.
Hudspeth R. L. et al., "Characterization and Expression of Chitinase and 1-3-β-Glucanase Genes in Cotton", Plant Molecular Biology vol. 31, No. 4, pp. 911-916, Apr. 1996.
Jiang et al., "Polyploid Formation Created Unique Avenues for Response to Selection in Gossypium (Cotton)", Proceedings of the National Academy of Sciences of the United States of America, vol. 95, pp. 4419-4424, Apr. 1998.
Ruan et al., "The Control of Single-Celled Cotton Fiber Elongation by Developmentally Reversible Gating of Plasmodesmata and Coordinated Expression of Sucrose and K+ Transporters and Expansin", The Plant Cell, vol. 13, pp. 47-60, Jan. 2001.
Ruan et al., "Gentypic and Developmental Evidence for the Role of Plasmodesmatal Regulation in Cotton Fiber Elongation Mediated by Callose Turnover", Plant Physiology, vol. 136, pp. 4104-4113, Dec. 2004.
Shimizu et al., "Changes in Levels of mRNAs for Cell Wall-Related Enzymes in Growing Cotton Fiber Cells", Plant and Cell Physiology vol. 38, No. 3, pp. 375-378, Jan. 1997.
Smeekens, "Sugar Regulation of Gene Expression in Plants", Current Opinion Plant Biology, vol. 1, pp. 230-234 (1998).
Sturm and Tang, "The Sucrose-Cleaving Enzymes of Plants are Crucial for Development, Growth and Carbon Partitioning", Trends in Plant Science—Reviews, vol. 4, pp. 401-407, Oct. 1999.

* cited by examiner

*Primary Examiner* — Elizabeth McElwain
(74) *Attorney, Agent, or Firm* — Hunton & Williams LLP

(57) ABSTRACT

Disclosed are methods and means to alter fiber properties such as fiber length in fiber producing plants such as cotton. Additionally plant promoters with a fiber-preferential or fiber-selective expression profile are provided.

17 Claims, 6 Drawing Sheets

FIGURE 1

```
  1 atgctgtttttaactcaactcctctctctaacagatggccgtgatattggtgttgctatggtttgaacggcaacaatcttcatctccaggagatgtta
  1 atggtgtttttaactcaactcctctctctaacagatggccgtgatattggtgttgctatggtttgaacggcaacaatcttccatctccaggagatgtta 101 ttaatctttttcaaaactagtggcataacaatatcaggctctacagccttacccgaagtgctcgaagcagcaagggatcggaatatccctctgat
101 ttaatctttttacaaaactagtggcataacaatatcaggctctacagccttacccgaagtgctcgaagcagcaagggatcggaatatccctctgat 201 gagtacgacaaacgaggacatacaaagcctcgcaacggatcaaagtgcagccgatgcatgggttaacaccaacatcgtccctataaggagatgttcaa
201 gggtcgagaaacgaggacatacaaagcctcgcaaaagatcaaagtgcagccgatgcatgggttaacaccaacatcgtccctataaggagatgttcag 301 ttcaggttcatcatcattgggaatgaagccattcaggacagtcaagctcttacattcctggtgccatgaacaacataatgaactcgctgcctcatttg
301 ttcaagttgatcactattgggaatgaagccattcaggacaatcaagctcttacattcctgatgccatgaacaacataatgaactcgctgccttatttg 401 ggctaggcacgacgaaggttacgaccggtgtcccgatgaatgccctaagtacctcgtacccctcctcagacggcgcttttgaagcgatataacatcgat
401 ggttaggcacgacgaaggttacgaccggtgtcccgatgaatgccctaagtacctcgtacccctcctcagacggcgcttttgaagcgatataacatcgat 501 catgactagtatcatggccattctggttcgacaggattcgccccctcctgatcaatgtgtacccttatttgcctcagacccccactcatatttcc
501 catgactagtatcatggccattctggtgtacaggattcgccccctcctgatcaatgtgtacccttatttgcctcagacccccactcatatttcc 601 ctcaactacgccttgttcacctcgaccgcaccggtggtgtcgaccaaggcttggaatactacaacctcttgacggcatggtcgatgctttcaatgccg
601 ctcgattacgccttgttcacctcgaccgcaccggtggtgtcgaccaaggcttggaatactacaacctcttgacggcatggtcgatgctttcaatgccg 701 ccctagataagatcggcttcggccaaattactctcattgtagcgaaactggatggccgaccgcggtaacgagccttacacgagtgtcgcgaacgctca
701 ccctagataagatcggcttcggccaaattactctcattgtagcgaaactggatggccgaccgcggtaacgagccttacacgagtgtcgcgaacgctca 801 aacttataacaagaacttgttgaatcatgtgacgcagaaagggactccgaaaagacctgaatataatgccgacgttttcttcgacgttttcaacgag
801 aacttataacaagaacttgttaatcatgtgacgcagaagggactccgaaaagacctgaatataatgccgacgttttcttcgagagttttcaacgag 901 aacttgaagcaacccacagttgagcagaatttcgattcttcttcccaatgaacctgtttatccatttggtga
901 gatttgaagcaacccacagttgagcagaatttcgattcttcttcccaatgaacctgtttatccatttggtga
```

FIGURE 2

```
  1  gtaaaacaaacttctctacagtgatttttacagtaaatatggctttgaaaaatatacaacaaaacatttatcttcaatccatttaattactgatctacta
  1  gtaaaacaaacttctctacagtgatttttacggtaagtatggctttgaaaaatatacaacaacaaacatttta-----------tactgatctacca 101  tatatgttgcag
 83  tatatgttgcag
```

FIGURE 3

```
  1 mlfltqllslltdgrdigvcyglngnnlpspgdvinlfktsginnirlyqpypevleaargsgislsmstthediqslatdqsaadawvntnivpykedvq
  1 mvfltqllslltdgrdigvcyglngnnlpspgdvinlyktsginnirlyqpypevleaargsgislsmgprnediqslakdqsaadawvntnivpykddvq 101 frfiiigneaipgqsssyipgamnnimnslasfglgttkvttvvpmnalstsyppsdgafgsditsimtsimailvrqdspllinvypyfayasdpthis
101 fklitigneaisgqsssyipdamnnimnslalfglgttkvttvvpmnalstsyppsdgafgsditsimtsimailavqdspllinvypyfayasdpthis 201 lhyalftstapvvvdqgleyynlfdgmvdafnaaldkigfgqitlivaetgwptagnepytsvanaqtynknllnhvtqkgtpkrpeyimptfffemfne
201 ldyalftstapvvvdqgleyynlfdgmvdafnaaldkigfgqitlivaetgwptagnepytsvanaqtynknllnhvtqkgtpkrpeyimptfffemfne 301 nlkqptveqnfgfffpnmnpvypfw
301 dlkqptveqnfgfffpnmnpvypfw
```

FIGURE 4

```
         GaGluc1#-#Garb#leaves#gDNA  CGGATCAAAGT
GhGluc1SGA#FiberMax966#Ghir#leaves#gDNA  CGGATCAAAGT
GhGluc1SGD#FiberMax966#Ghir#leaves#gDNA  AAGATCAAAGT
         GrGluc1#-#Grai#leaves#gDNA  AAGATCAAAGT
```

FIGURE 5

DIFFERENTIAL EXPRESSION OF SUBGENOME SPECIFIC ALLELES IN COTTON AND USES THEREOF

CROSS-REFERENCE TO RELATED APPLICATIONS

This application is the U.S. National Stage filing of International Application No. PCT/EP2008/000161, filed Jan. 7, 2008, which claims priority to European Patent Application No. EP 07000550.9, filed Jan. 11, 2007, and U.S. Provisional Application No. 60/884,564, filed Jan. 11, 2007, the disclosures of which are hereby incorporated in their entirety by reference.

FIELD OF THE INVENTION

This invention relates to the field of agriculture, more specifically towards the use of molecular biology techniques to alter fiber producing plants, particularly cotton plants and/or accelerate breeding of such fiber containing plants. Methods and means are provided to alter fiber qualities such as increasing fiber length, particularly lint fiber length or to decrease the length of fuzz fibers. Methods are also provided to identify molecular markers associated with fiber length in a population of cotton varieties and related progenitor plants. Furthermore, plant promoters with a fiber-preferential or fiber-selective expression profile are provided. The promoters are also temporarily regulated.

BACKGROUND ART

Cotton provides much of the high quality fiber for the textile industry. The modification of cotton fibers characteristics to better suit the requirements of the industry is a major effort in breeding by either classical methods or by genetically altering the genome of cotton plants.

About 90% of cotton grown worldwide is *Gossypium hirsutum* L., whereas *Gossypium barbadense* accounts for about 8%. As in most flowering plants, cotton genomes are thought to have incurred one or more polyploidization events and to have evolved by the joining of divergent genomes in a common nucleus. The cotton commerce is dominated by improved forms of two "AD" tetraploid species, *Gossypium hirsutum* L. and *Gossypium barbadense* L. Tetraploid cottons are thought to have formed about 1-2 million years ago, in the New World, by hybridization between a maternal Old World "A" genome taxon resembling *Gossypium herbaceum* and paternal New World "D" genome taxon resembling *Gossypium raimondii* or *Gossypium gossypioides*. Wild A genome diploid and AD tetraploid *Gossypium taxa* produce spinnable fibers. One A genome diploids species, *Gossypium arboreum*, remains intensively bred and cultivated in Asia. Its close relative and possible progenitor, the A genome diploid species *G. herbaceum* also produces spinnable fiber. Although the seeds of D genome diploids are pubescent, none produce spinnable fibers. No taxa from the other recognized diploid *Gossypium* genomes (B, C, E, F, and G) have been domesticated. Intense directional selection by humans has consistently produced AD tetraploid cottons that have superior yield and/or quality characteristics compared to the A genome diploid cultivars. Selective breeding of *G. hirsutum* (AADD) has emphasized maximum yield, whereas *G. barbadense* (AADD) is prized for its fibers of superior length, strength, and fineness (Jiang et al. 1998—Proc Natl Acad Sci USA. 1998 Apr. 14; 95(8): 4419-4424).

A cotton fiber is a single cell that initiates from the epidermis of the outer integument of the ovules, at or just prior to anthesis. Thereafter, the fibers elongate rapidly for about 3 weeks before they switch to intensive secondary cell wall cellulose synthesis. Fiber cells interconnect only to the underlying seed coat at their basal ends and influx of solute, water and other molecules occurs through either plasmodesmata or plasma membrane. Ruan et al. 2001 (Plant Cell 13: 47-63) demonstrated a transient closure of plasmodesmata during fiber elongation. Ruan et al. 2004 (Plant Physiology—Vol 136: pp. 4104-4113) compared the duration of plasmodesmata closure among different cotton genotypes differing in fiber length and found a positive correlation between the duration of the plasmodesmata closure and fiber length. Furthermore, microscopic evidence was presented showing callose deposition and degradation at the fiber base, correlating with the timing of plasmodesmata closure and reopening. Furthermore, expression of a $\beta$-1,3-endoglucanase gene (Gh-Gluc1) in the fibers, allowing to degrade callose, correlated with the reopening of the plasmodesmata at the fiber base.

WO2005/017157 describes methods and means for modulating fiber length in fiber producing plants such as cotton by altering the fiber elongation phase as described in Ruan et al 2001. The fiber elongation phase may be increased or decreased by interfering with callose deposition in plasmodesmata at the base of the fiber cells.

Furthermore, it would be interesting for modification of fibers through genetic engineering, to possess promoters which are preferentially or specifically expressed in fibers cells only, and/or which are expressed only from a particular fiber development stage on.

WO2004/018620 relates to an isolated nucleic acid molecule encoding an endogenous cotton chitinase and its promoter, which are preferentially expressed in fibers during secondary wall deposition. The polypeptide encoded by the nucleic acid molecule, a DNA construct linking the isolated nucleic acid molecule with a promoter, the DNA construct incorporated in an expression system, a host cell, a plant, or a plant seed are also disclosed. The document also relates to a DNA construct linking the isolated promoter with a second DNA as well as expression systems, host cells, plants, or plant seeds containing the DNA construct. Methods of imparting resistance to insects and fungi, regulating the fiber cellulose content, and methods of expressing a gene preferentially in fibers during secondary wall deposition are also disclosed.

It would be useful to have alternative promoters that would drive gene expression preferentially and/or strongly in fibers throughout secondary wall deposition, i.e., strongly and continuously (e.g. at >50% of its maximal activity) e.g. from the initiation of secondary wall deposition to its termination or e.g. from maturation stage on. The initiation of secondary wall deposition is defined as the time when the dry weight/unit length of a cotton fiber begins to increase or when the dry weight/unit surface area of any cell begins to increase via synthesis of new wall material containing more than 40% (w/w) of cellulose. In the case of cotton fiber of *G. hirsutum* L., this is expected to occur between 14-17 DPA when cotton plants are grown under typical conditions in the greenhouse or the field (day temperature of 26-34° C., night temperature of 20-26° C., light intensity greater than or equal to 1000 einsteins/m$^2$/s, with adequate water and mineral nutrition). The end of the secondary cell wall formation and start of the maturation phase is usually around 35DPA in the case of cotton fiber of *G. hirsutum* L.

Furthermore, it would be useful to have alternative promoters that would drive gene expression only or preferentially in fibers while excluding or minimizing expression in other tissues.

The inventions described hereinafter in the different embodiments, examples, figures and claims provide improved methods and means for modulating fiber length by decreasing or increasing callose deposition at the base of the fiber cell at a particular time point. The inventions described hereinafter also provide fiber-specific and/or fiber-preferential promoters and promoter regions.

SUMMARY OF THE INVENTION

In one embodiment of the invention, a fiber cell preferential promoter is provided comprising a nucleotide sequence selected from the following group of nucleotide sequences:
a) a nucleotide sequence comprising the nucleotide sequence of SEQ ID No 9 from the nucleotide at position 2149 to the nucleotide at position 2307;
b) a nucleotide sequence comprising the nucleotide sequence of SEQ ID No 10 from the nucleotide at position 3109 to the nucleotide at position 3269;
c) a nucleotide sequence comprising the nucleotide sequence having at least 70% preferably at least 80%, more preferably at least 90%, particularly at least 95% sequence identity with or, more particularly is identical to any of the nucleotide sequence mentioned under a) or b) or
d) a nucleotide sequence comprising the nucleotide sequence of an about 150 bp to an about 1000 bp DNA fragment hybridizing under stringent conditions with a DNA fragment having the nucleotide sequence mentioned under a), b) or c).

The fiber cell preferential promoter may comprise the nucleotide sequence of SEQ ID No 9 from position 465 to position 2307; or the nucleotide sequence of SEQ ID No 9 from position 1374 to position 2307; or the nucleotide sequence of SEQ ID No 9 from position 1531 to position 2307; or the nucleotide sequence of SEQ ID No 10 from position 1397 to position 3269; or the nucleotide sequence of SEQ ID No 10 from position 2371 to position 3269; or the nucleotide sequence of SEQ ID No 10 from position 2718 to position 3269.

In another embodiment, the invention provides a fiber cell preferential promoter region comprising a fiber cell preferential promoter as herein described further comprising the nucleotide sequence of SEQ ID 9 from the nucleotide at position 2308 to the nucleotide at position 2409 or the nucleotide at position 3270 to the nucleotide at position 3372.

In yet another embodiment of the invention, a chimeric gene is provided comprising the following operably linked DNA regions
a) a fiber cell preferential promoter as herein described;
b) a heterologous DNA region encoding a biologically active RNA of interest; and
c) a transcription termination and polyadenylation signal.

The biologically active RNA may encode a protein of interest, such as a N-acetylglucosamine transferase, preferably an N-acetylglucosamine transferase of the NodC type, a cellulose synthase, a sucrose synthase, preferably a sucrose synthase of the C-type; a sucrose phosphate synthase or a β-1,3-endoglucanase. The biologically active RNA may also be an inhibitory RNA or silencing RNA such as a ribozyme, microRNA, double stranded hairpin RNA, particularly targeted to downregulate the expression of an endogenous cotton gene, such as β-1,3-endoglucanase xylan synthase (cslF) xyloglucan synthase (cslD) or 1,3-1,4 glucan synthase (cslC).

Also provided are plant cell and plants, such as cotton plants, and seeds thereof, comprising such chimeric genes. A seed of a plant comprising in its cells a chimeric gene according to any one of claims 11 to 15.

The invention further provides a method for expressing a biologically active RNA preferentially in a fiber cell of a fiber producing plant, such as a cotton plant, the method comprising the steps of providing the cells of the plants with a chimeric gene according to the invention and growing the plants.

In yet another embodiment, the invention is directed at the use of a fiber-specific and/or fiber-preferential promoter according to the invention for preferential expression of a biologically active RNA in fiber cells of a fiber-producing plant such as a cotton plant.

The invention further provides an isolated DNA molecule comprising a nucleotide sequence encoding a protein comprising an amino acid sequence having at least 95% sequence identity, preferably is identical, to the amino acid sequence of SEQ ID No 11 or SEQ ID No 12 and encoding a β-1,3-endoglucanase; an isolated DNA molecule comprising a nucleotide sequence selected from the group of SEQ ID No 1; SEQ ID No 2, SEQ ID No 3 and SEQ ID No 4 or an isolated DNA molecule comprising a nucleotide sequence selected from the nucleotide sequence of SEQ ID No 9 from position 2410 to 2443 and the nucleotide sequence of SEQ ID No 9 from position 2556 to 3499 or the nucleotide sequence of SEQ ID No 10 from position 3373 to 3406 and the nucleotide sequence of SEQ ID No 10 from position 3501 to 4444. These isolated DNA molecules may be used for isolation of a fiber cell preferential promoter or promoter region.

The invention also provides a method for isolating a fiber cell preferential promoter region, comprising the steps of:
identifying a genomic fragment encoding an RNA transcript from which a cDNA can be synthesized, the cDNA comprising the nucleotide sequence of SEQ ID 1, SEQ ID No 2, SEQ ID 3 or SEQ ID No 4 or functional equivalents thereof;
isolating a DNA region upstream of a nucleotide sequence encoding the protein with the amino acid of SEQ ID No 11 or SEQ ID No 12 or functional equivalents thereof.
Also provided are fiber selective promoters and promoter regions obtained by this method.

According to a second aspect of the invention, a method is provided for altering the properties of a fiber in a fiber producing plant, particularly increasing the length of a fiber of a cotton plant, comprising the step of introducing a chimeric gene into a cell of the cotton plant, the chimeric gene comprises the following operably linked DNA elements:
(a) a plant expressible promoter, preferably a plant expressible promoter which controls transcription preferentially in the fiber cells such as a fiber-specific beta tubulin promoter from cotton, a fiber-specific actin promoter from cotton, a fiber specific promoter from a lipid transfer protein gene from cotton, a promoter from an expansin gene from cotton or a promoter from a chitinase gene in cotton or a promoter as herein described;
(b) a transcribed DNA region, which when transcribed yields a biologically active RNA molecule capable of reducing the expression of a β-1,3 endoglucanase encoding gene endogenous to the fiber producing plant, the β-1,3 endoglucanase being involved in callose removal from the plasmodesmata and
(c) a 3' end region comprising transcription termination and polyadenylation signals functioning in cells of the plant, characterized in that only the expression of a specific subgenomic allele of the endogenous β-1,3 endoglucanase encoding gene is downregulated. In a preferred embodiment that β-1,3 endoglucanase encoding gene comprised within the D subgenome of the cotton plant. The β-1,3 endoglucanase encoding gene comprised within the D subgenome may be characterized by the presence of an intron sequence having the nucleotide sequence of SEQ ID No 10 from position 3407 to 3500 or may be characterized by the presence of a nucleotide sequence AAGATC about 326 nucleotides downstream the translation initiation codon (and not including that translation initiation codon). Conveniently, the β-1,3 endoglucanase encoding gene comprised within the D subgenome may be characterized the identification of an about 538 bp fragment and an about 118 bp fragment after PCR amplification with oligonucleotides having the nucleotide sequence of SEQ ID No 5 and SEQ ID no 6 followed by digestion with AlwI restriction enzyme. The β-1,3 endoglucanase encoding gene may also be encoding a protein comprising the amino acid sequence of SEQ ID No 12 or wherein the gene comprises the nucleotide sequence of SEQ ID No 2. The cotton plant may be *Gossypium hirsutum*.

The biologically active RNA may be an antisense RNA comprising at least 19 nucleotides having at least 94% sequence identity to the complement of nucleotide sequence of SEQ ID No 3 or a sense RNA comprising at least 19 nucleotides having at least 94% sequence identity to the nucleotide sequence of SEQ ID No 3 or a double stranded RNA molecule comprising at least 19 nucleotides having at least 94% sequence identity to the complement of the nucleotide sequence of SEQ ID No 3 and a complementary RNA strand essentially similar to the complement of the at least 19 nucleotides. Preferably, the mentioned 19 nucleotides comprises at least one nucleotide specific for the D subgenome Ghgluc1 gene as indicated in FIG. 2. In yet another embodiment according to the invention, double stranded RNA is micro RNA processed from a pre-microRNA comprising the nucleotide sequence of SEQ ID No 15, SEQ ID No 16, SEQ ID No 20 or SEQ ID No 21.

The invention also provides a method for decreasing the length of a fiber of a fiber producing plant, comprising the step of introducing a chimeric gene into a cell of the fiber producing plant wherein the chimeric gene comprises the following operably linked DNA fragments:
  (a) a plant-expressible promoter according to claims 1b, 5, 6 or 7;
  (b) a DNA region encoding a β-1,3 glucanase protein such as a protein having an amino acid sequence having at least 95% sequence identity to the amino acid sequence of SEQ ID No 11 or SEQ ID No 12; and
  (c) a 3'end region comprising transcription termination and polyadenylation signals functioning in cells of the plant.

Yet another embodiment of the invention concerns a chimeric gene as herein described or a cell of a fiber-producing plant or a fiber producing plant comprising such chimeric gene In still another embodiment, the invention provides fibers produced according to the methods herein described.

BRIEF DESCRIPTION OF THE FIGURES

FIG. 1: alignment of promoter regions of the β-1,3-endoglucanase gene from subgenome A and from subgenome D of *Gossypium hirsutum*. The nucleotide sequence of promoter of subgenome A (upper sequence) corresponds to the nucleotide sequence of SEQ ID No 9 from position 1460 to position 2408. The nucleotide sequence of promoter of subgenome D (lower sequence) corresponds to the nucleotide sequence of SEQ ID No 10 from position 2372 to position 3372. Differences in nucleotide sequence are indicated by gray boxes. Nucleotides which do not have a corresponding nucleotide in the other promoter region are indicated by dashes in the nucleotide sequence missing the nucleotides. Overall homology between the two promoter regions is about 71% sequence identity.

FIG. 2: alignment of coding regions of the β-1,3-endoglucanase gene (without intron) from subgenome A and from subgenome D of *Gossypium hirsutum*. The nucleotide sequence of coding region of subgenome A allele (upper sequence) corresponds to the nucleotide sequence of SEQ ID No 9 from position 2410 to position 2443 and from position 2556 to 3499. The nucleotide sequence of coding region of subgenome D allele (lower sequence) corresponds to the nucleotide sequence of SEQ ID No 10 from position 3373 to position 3406 and from position 3501 to 4444. Differences in nucleotide sequence are indicated by gray boxes. Nucleotides which do not have a corresponding nucleotide in the other promoter region are indicated by dashes in the nucleotide sequence missing the nucleotides. Overall homology between the two promoter regions is about 97% sequence identity.

FIG. 3: alignment of the intron sequence from the β-1,3-endoglucanase gene from subgenome A and from subgenome D of *Gossypium hirsutum*. Upper sequence corresponds to the nucleotide sequence of the subgenome A allele intron, while the lower sequence corresponds to the nucleotide sequence of the subgenome D allele intron.

FIG. 4: alignment of the amino acid sequence of the β-1,3-endoglucanase encoded by the subgenome A allele (upper sequence corresponding to SEQ ID No 11) and subgenome D allele (lower sequence corresponding to SEQ ID No 12).

FIG. 5: alignment of the nucleotide sequence of SEQ IDs 1 to 4 from nucleotide position 201 to 211. The Alw1 restriction enzyme recognition site present in the nucleotide sequence of the subgenome A allele only of the β-1,3-endoglucanase gene is underlined and represented in italics.

DETAILED EMBODIMENTS

Figure 6:
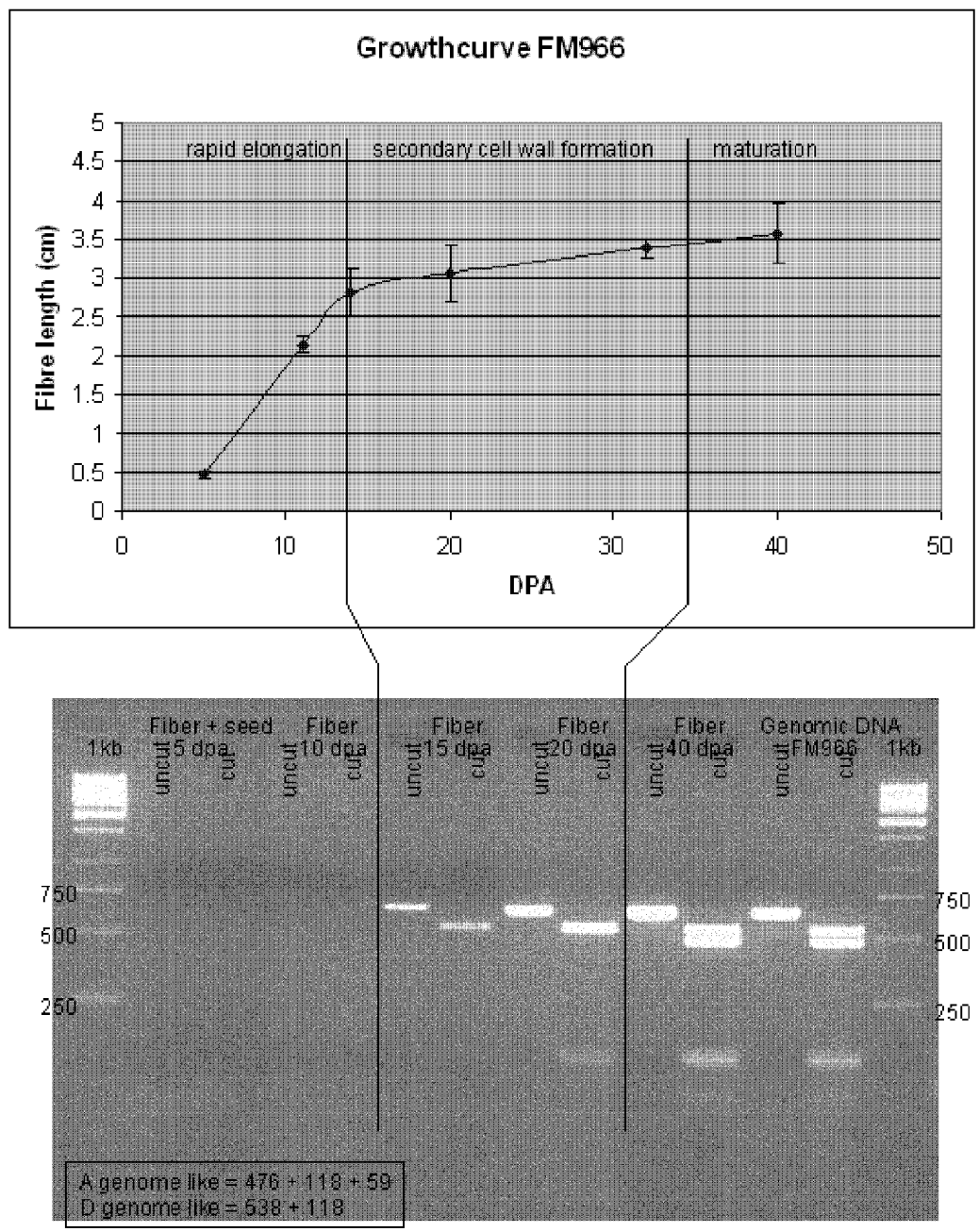
FIG. 6: Correlation between fiber growth curve (panel A) and expression of the β-1,3-endoglucanase gene (GhGluc1) (panel B). DNA from a cDNA library from (developing) fibers in *Gossypium hirsutum* was extracted and equalized. PCR fragments were amplified using oligonucleotide primers SE002 and SE003 (SEQ ID No 5 and 6) and digested with AlwI. A PCR amplified product for the A-genome variant yields 3 fragments (479 bp+118 bp+59 bp) while for the D-genome variant it only yields 2 fragments (538 bp+118 bp).

The current invention is based on the unexpected finding that the timing of expression of the A and D subgenome specific alleles of the fiber specific β-1,3-endoglucanase gene (GhGluc1) is different at least in Gossypium hirsutum. Whereas the onset of the expression of the D subgenome specific allele correlates with the end of the rapid elongation phase (about 14 to 17 days post-anthesis hereinafter "DPA"), onset of the expression of the A subgenome is delayed until the beginning of the late fiber maturation phase (about 35-40 DPA) depending on growth conditions.

Accordingly, in one aspect, the current invention relates to the identification of novel fiber-specific promoters which either are expressed preferentially in fiber cells from the end of the rapid elongation phase or from the onset of the fiber maturation phase. Such promoters have a utility e.g. in the expression of novel biomolecule producing chimeric genes at late fiber development stages, for example encoding enhanced XET, Cellulose Binding Domain (CBD), Root Swollen (RSW) mutant genes, coloring, plastics, cellulose digestibility, novel cell wall composites/properties. The promoters could also be used to direct gene expression at 20, 30, 40 DPA in fibers; for example production of chitin in late stages of cotton fiber development (20, 30, 40 DPA) or for gene expression at 40DPA in fibers for example production of chitin in very late stages of cotton fiber development (40 DPA). The promoters according to the invention could also be used to direct expression of CesA genes at 40DPA for enhanced cellulose biosynthesis and enhanced fiber properties or to produce biologically active RNA directed at stage specific silencing of endogenous cotton genes, such as silencing β-1,3-endoglucanase for longer fiber growth. The promoters could also be applied in the stage specific expression of chimeric genes encoding e.g. callose synthase to alter fiber properties and quality.

In another aspect, the current invention is directed towards the silencing of the expression of one subgenome specific allele of the fiber specific β-1,3-endoglucanase gene, particularly silencing of the D-subgenome specific allele, to prevent callose degradation and thus increase the rapid fiber elongation phase and the fiber length e.g. in cotton, particularly in Gossypium hirsutum.

According to one embodiment of the first aspect of the invention, the invention provides a fiber-specific and/or fiber-preferential promoter fragment which can be isolated from cotton, particularly from Gossypium hirsutum species, and which is located upstream of the nucleic acid sequences encoding a fiber specific β-1,3-endoglucanase having an amino acid sequence comprising the amino acid sequence of SEQ ID 11, 12, 7 or 8 or variants thereof.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

The term "regulatory region", as used herein, means any DNA, that is involved in driving transcription and controlling (i.e., regulating) the timing and level of transcription of a given DNA sequence, such as a DNA coding for a protein or polypeptide. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription 3' end formation (and/or regulation) signals, including one or more polyadenylation signals.

The term "gene" means any DNA fragment comprising a DNA region (the "transcribed DNA region") that is transcribed into a RNA molecule (e.g., a mRNA) in a cell under control of suitable regulatory regions, e.g., a plant expressible promoter region. A gene may thus comprise several operably linked DNA fragments such as a promoter, a 5' untranslated leader sequence, a coding region, and a 3' untranslated region comprising a polyadenylation site. An endogenous plant gene is a gene which is naturally found in a plant species. A chimeric gene is any gene which is not normally found in a plant species or, alternatively, any gene in which the promoter is not associated in nature with part or all of the transcribed DNA region (a "heterologous" DNA region) or with at least one other regulatory regions of the gene.

The term "expression of a gene" refers to the process wherein a DNA region under control of regulatory regions, particularly the promoter, is transcribed into an RNA which is biologically active i.e., which is either capable of interaction with another nucleic acid or which is capable of being translated into a biologically active polypeptide or protein. A gene is said to encode an RNA when the end product of the expression of the gene is biologically active RNA, such as an antisense RNA or a ribozyme. A gene is said to encode a protein when the end product of the expression of the gene is a functionally or biologically active protein or polypeptide.

The term "fiber-selective" or "fiber cell selective" or "fiber specific" or "fiber cells specific", with respect to the expression of a DNA in accordance with this invention, refers to, for practical purposes, the highly specific, expression of a DNA in fiber cells of plants, such as cotton plants ("fiber cell-selective"). In other words, transcript levels of a DNA in tissues different of fiber cells is either below detection or very low (less than about 0.2 pico grammes per microgram total RNA).

The term "fiber-preferential" or "fiber-cell preferential" with respect to the expression of a DNA in accordance with this invention, refers to an expression pattern whereby the DNA is expressed predominantly in fiber cells or fibers, but expression can be identified in other tissues of the plant. Preferably, the expression in fiber cells is about 2 to about 10 times higher in the fiber cells than in other tissues.

The nucleotide sequences of SEQ ID No 9 and SEQ ID No 10 represent the nucleotide sequences of genomic DNA molecules encoding respectively a fiber selective β-1,3 endoglucanase of the A subgenome and of the D subgenome. The transcription initiation site of SEQ ID No 9 has been determined at position 2308, while the transcription initiation site of SEQ ID No 10 has been determined at position 3270. Thus in one embodiment of the invention a fiber selective promoter is provided having the nucleotide sequence of SEQ ID No 9 from nucleotide position 1 to nucleotide position 2307 or 2308; in another embodiment of the invention a fiber selective promoter is provided having the nucleotide sequence of SEQ ID No 10 from nucleotide position 1 to nucleotide position 3269 or 3270.

The translation initiation site of the nucleotide sequence of SEQ ID No 9 has been determined as the ATG codon located at positions 2410 to 2412. The 5'untranslated region of the fiber selective promoter of the A subgenomic allele encoding β-1,3 endoglucanase accordingly has a nucleotide sequence of SEQ ID No 9 from nucleotide position 2308 to nucleotide position 2409. A fiber selective promoter region of the A subgenomic allele is accordingly a promoter region comprising nucleotides 1 to 2409 of SEQ ID No 9.

Likewise, the translation initiation site of the nucleotide sequence of SEQ ID No 10 has been determined as the ATG codon located at positions 3373 to 3375. The 5'untranslated region of the fiber selective promoter of the D subgenomic allele encoding β-1,3 endoglucanase accordingly has a nucleotide sequence of SEQ ID No 10 from nucleotide position 3270 to nucleotide position 3372. A fiber selective promoter region of the D subgenomic allele is accordingly a promoter region comprising nucleotides 1 to 3372 of SEQ ID No 10.

Figure 1:
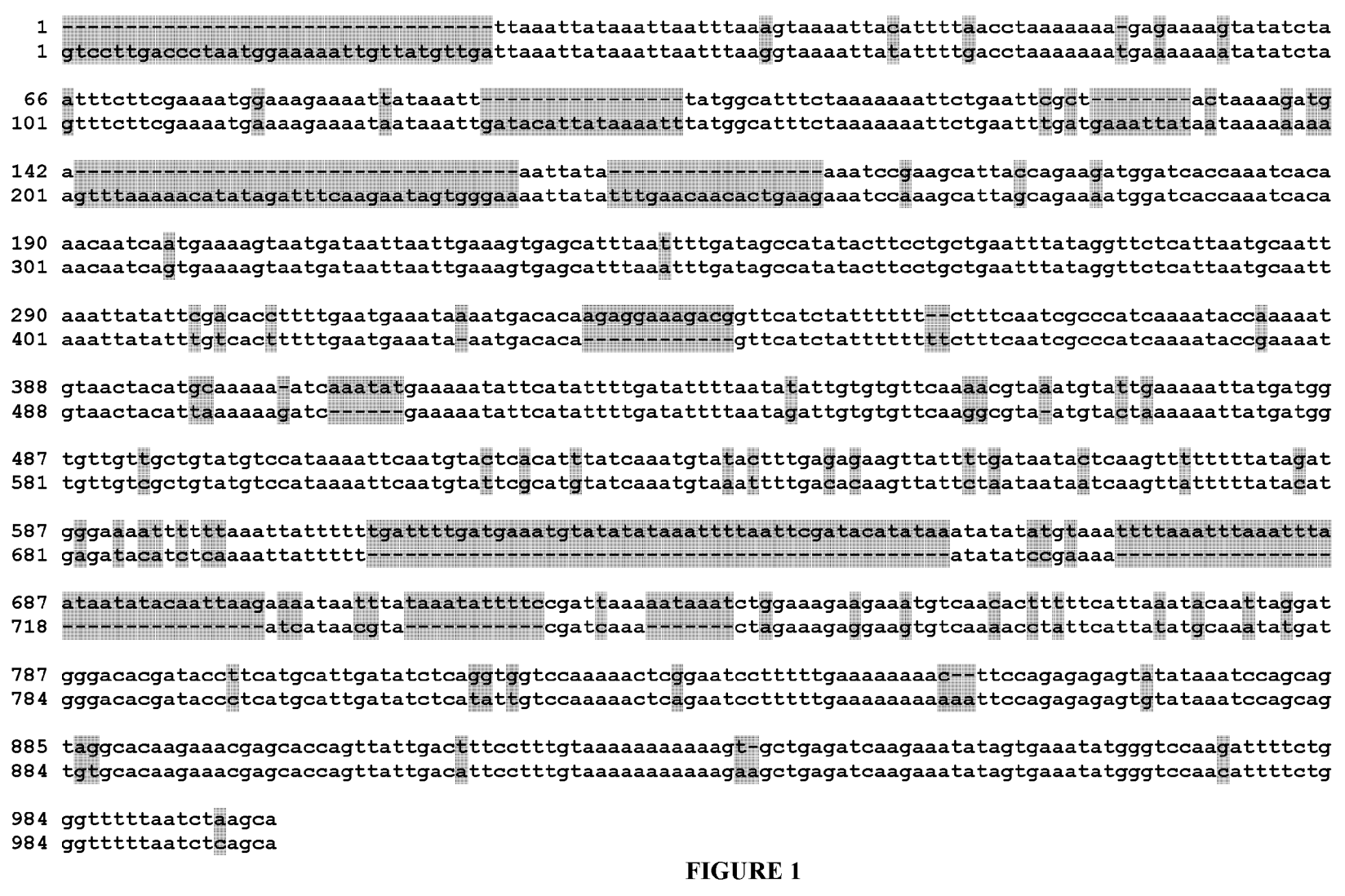

Alignment of the fiber selective promoters regions of SEQ ID No 9 and SEQ ID No 10 (FIG. 1) revealed a general sequence homology in the nucleotide sequences about 1000 nucleotides upstream from the ATG translation initiation codon, particularly in the region about 150 nucleotide upstream from the ATG translation initiation codon. Thus, in another embodiment of the invention, a fiber-selective promoter is provided comprising the nucleotide sequence of SEQ ID No 9 from nucleotide position 2149 to nucleotide position 2307 or comprising the nucleotide sequence of SEQ ID No 10 from nucleotide position 3109 to nucleotide position 3269.

It goes without saying that promoter or the promoter region may be contained within larger nucleotide sequences. A fiber cell selective promoter region can thus be determined as the region upstream (i.e., located 5' of) from the codon coding for the first amino acid of the protein encoded by the mRNA indicated in SEQ ID No 9 or 10. Such a promoter region may be at least about 400 to 500 bp, at least about 1000 bp, at least 1200 bp, at least about 1300 bp, or at least about 1500 to 2000 bp, upstream of the start codon. For convenience, it is preferred that such promoter region does not extend more than about 3000 to 5000 bp upstream of the start codon. The size fragment may be partially determined by the presence of convenient restriction sites. E.g. for the fiber selective promoter region of the A subgenome allele encoding β-1,3 endoglucanase, a fragment of about 1945 bp (from nucleotide position 465 to nucleotide position 2409 of SEQ ID No 9) can be conveniently cloned. The presence of suitable restriction enzymes allows to conveniently generate promoter regions of about 1036 bp (from nucleotide 1374 to nucleotide position 2409 of SEQ ID No 9) or of about 879 np (from nucleotide 1531 to nucleotide position 2409 of SEQ ID No 9). For the fiber selective promoter region of the D subgenome allele encoding β-1,3 endoglucanase, a fragment of about 1976 bp (from nucleotide position 1397 to nucleotide position 3372 of SEQ ID No 10) can be conveniently cloned. The presence of suitable restriction enzymes allows to conveniently generate promoter regions of about 1002 bp (from nucleotide 1397 to nucleotide position 3372 of SEQ ID No 10) or of about 655 np (from nucleotide 2371 to nucleotide position 3372 of SEQ ID No 10).

Applicant has deposited 1 plasmid (pDBl153) comprising the A subgenome 1.9 kb promoter of the glucanase gene in a pUC19 based vector with the BCCM/LMPB Belgian coordinated Collections of Micro-organisms, LMBP Plasmid Collection, Ghent University—Department of Biomedical Molecular biology, Technologiepark 927, 9052 Gent-Zwijnaarde, Belgium, under Accession No. LMBP 8351. The plasmid was deposited with the BCCM/LMPB on May 2, 2013, under the Budapest Treaty. Access to this deposit will be available during the pendency of the application to the Commissioner of Patents and Trademarks and persons determined by the Commissioner to be entitled thereto upon request. The deposit will be maintained for a period of 30 years, or 5 years after the most recent request, or for the enforceable life of the patent, whichever is longer, and will be replaced if it becomes nonviable during that period. Applicant does not waive any rights granted under this patent or under the Plant Variety Protection Act (7 U.S.C. 2321 et seq.).

It will further be clear that equivalent fiber selective promoters or promoter regions can be isolated from other cotton plants or cotton progenitor plants. To this end, promoter fragments may be isolated from other cotton plants, such a G. barbadense including the so-called PIMA varieties, or from other varieties using a promoter fragment as herein described as a probe and identifying nucleotide sequences from these other plants which hybridize under stringent hybridization conditions.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

Such equivalent fiber selective promoters isolated from other cotton plants or cotton progenitor plants may represent variant promoters wherein one or more nucleotides have been replaced by substitution, deletion or insertion. Variant fiber selective promoter according to the invention may also be generated synthetically. FIG. 1 represents the alignment of fiber selective promoters from the A and D subgenome of G. hirsutum and variant positions, where the nucleotide sequence may be apparently changed without a significant effect on the fiber selective transcription initiation capacity, have been indicated by gray boxes. From FIG. 1 and its legend, it also apparent that the overall sequence identity between the two exemplified fiber selective promoter fragments may be as low as about 71% sequence identity.

Accordingly, in another embodiment of the current invention, fiber selective promoter and promoter regions are provided which comprise a nucleotide sequence having at least 70%, or at least 80%, or at least 90% or at least 95% sequence identity to the herein described fiber selective promoters and promoter regions.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

Fiber selective expression capacity of the identified or generated promoter or promoter regions can be conveniently tested by operably linking such DNA molecules to a coding region encoding an easily scorable marker, e.g. a β-glucuronidase gene, introducing such a chimeric gene into a fiber producing plant, and analyzing the expression pattern of the marker in fiber cells (preferably during fiber development) in comparison with the expression pattern of the marker in other parts of the plants.

It goes without saying that promoters and promoter regions of the invention may also comprise additional elements known to improve transcription efficiency such as enhancers, introns, etc.

Further, the exemplified 5' UTR sequences of the exemplified fiber selective promoter regions are rather similar in nucleotide sequence, and it is expected that the 5'UTR sequences are interchangeable.

The invention further includes DNA molecules comprising the fiber selective promoters or promoter regions of the invention operably linked to one or more heterologous regions coding for a biologically active RNA, peptide or protein. The promoters of the invention may be used to express any heterologous coding region desired.

Examples of other protein-encoding DNA molecules that could be expressed using the promoter of the current invention include, but are not limited to, homologous and heterologous cellulose synthases (CesA genes), both in normal and mutated form (Arioli et al., "Molecular Analysis of Cellulose Biosynthesis in Arabidopsis," Science, 279: 717-720 (1998); Holland et al., "A Comparative Analysis of the Plant Cellulose Synthase (CesA) Gene Family," Plant Physio., 123: 1313-1324 (2000)); genes that may modulate carbon partitioning to cellulose (Delmer, "Cellulose Biosynthesis in Developing Cotton Fibers" in: A. S. Basra (ed.), Cotton Fibers: Developmental Biology Quality Improvement, and Textile Processing, The Haworth Press, New York, pp. 85-112 (1999)) such as sucrose synthase (Amor et al., "A Membrane-Associated Form of Sucrose Synthase and Its Potential Role Synthesis of Cellulose and Callose in Plants," Proc. Natl. Acad. Sci. USA, 92: 9353-9357 (1995), sucrose phosphate synthase (Haigler et al., "Transgenic Cotton Over-Expressing Sucrose Phosphate Synthase Produces Higher Quality Fibers with Increased Cellulose Content and Has Enhanced Seed Cotton Yield" Abstract 477. In: Proceedings of Plant Biology 2000, July 15-19, San Diego, Calif. American Society of Plant Physiologists, Rockville, Md., (2000), UDPG-pyrophosphorylase (Waffler and Meier, "Enzyme Activities in Developing Cotton Fibers," Plant Physiol. Biochem. 32: 697-702 (1994), inorganic pyrophosphatase (Geigenberger et al., "Overexpression of Pyrophosphatase Leads to Increased Sucrose Degradation and Starch Synthesis, Increased Activities of Enzymes for Sucrose-Starch Interconversions, and Increased Levels of Nucleotides in Growing Potato Tubers," Planta, 205:428-437 (1998)), hexokinases (Smeekens, "Sugar Regulation of Gene Expression" Curr. Op. Plant Biol., 1: 230-234 (1998), and invertases (Sturm and Tang, "The Sucrose-Cleaving Enzymes of Plants are Crucial for Development, Growth, and Carbon Partitioning," Trends Plant Sci., 4: 401-407 (1999)); genes that might affect the molecular and biophysical properties of cellulose including degree of polymerization, degree of crystallinity, crystallite size, and micro fibril orientation (i.e. genes for encoding proteins, including co-crystallizing protein polymers or cellulose binding domains, and polysaccharide-synthesizing and other enzymes) (Delmer, "Cellulose Biosynthesis: Exciting Times for a Difficult Field of Study," Ann. Rev. Plant Physio. Mol. Biol. 50: 245-276 (1999); Delmer, "Cellulose Biosynthesis in Developing Cotton Fibers. In: A. S. Basra (ed.), Cotton Fibers: Developmental Biology, Quality Improvement, and Textile Processing, The Haworth Press, New York, pp. 85-112 (1999); Hsieh, "Structural Development of Cotton Fibers. In: A. S. Basra (ed.), Cotton Fibers: Developmental Biology, Quality Improvement, and Textile Processing, The Haworth Press, New York, pp. 137-166 (1999)); transcription factors such as MYB genes that could prolong elongation growth and/or change the timing or extent of secondary wall deposition (Wilkins and Jernstedt, "Molecular Genetics of Developing Cotton Fibers. In: A. S. Basra (ed.), Cotton Fibers: Developmental Biology. Quality Improvement, and Textile Processing, The Haworth Press, New York, pp. 231-270 (1999)); genes to effect the synthesis of plant hormones and change fiber properties (John, "Genetic Engineering Strategies for Cotton Fiber Modification. In: A. S. Basra (ed.), Cotton Fibers: Developmental Biology, Quality Improvement, and Textile Processing, The Haworth Press, New York, pp. 271-289 (1999)); genes for cytoskeletal elements or cytoskeletal-associated proteins that might affect fiber properties (Seagull, "Cytoskeletal Involvement in Cotton Fiber Growth and Development," Micron, 24: 643-660 (1993)); genes for lipid synthesizing or modifying enzymes that might change membrane properties and thereby improve fiber quality, including under stressful environmental conditions (Haigler, "The Crystallinity of Cotton Cellulose in Relation to Cotton Improvement," Proc. Cotton Fiber Cellulose: Structure. Function and Utilization Conference, National Cotton Council of America: Memphis, Tenn., p. 211-225 (1992)); enzymes such as xyloglucan endotransferase, peroxidase, expansin, or vacuolar ATPase that might, through increased or decreased activity, prolong or increase extension growth during secondary wall deposition (Wilkins and Jernstedt, "Molecular Genetics of Developing Cotton Fibers. In: A. S. Basra (ed.), Cotton Fibers Developmental Biology Quality Improvement, and Textile Processing, The Haworth Press, New York, pp. 231-270 (1999); genes for protein or plastic polymers that might be retained in the fiber lumen or integrated into the cell wall to increase fiber strength or change its textile properties (John, "Genetic Engineering Strategies for Cotton Fiber Modification," In: A. S. Basra (ed.), Cotton Fibers: Developmental Biology. Quality Improvement, and Textile Processing, The Haworth Press, New York, pp. 271-289 (1999); Guda et al., "Hyperexpression of an Environmentally Friendly Synthetic PolymerGene," BiotechnologY Letters, 17: 745-750 (1995)); genes for plant cell wall matrix biosynthetic enzymes or their regulatory proteins so that other carbohydrates could be integrated into the cell wall and change fiber properties (Haigler, "The Relationship Between Polymerization and Crystallization in Cellulose Biogenesis," in C. H. Haigler and P. Weimer, eds., Biosynthesis and Biodegradation of Cellulose, New York: Marcel Dekker, pp. 99-124 (1991); Andrawis et al., "Cotton Fiber Annexins: A Potential Role in the Regulation of Callose Synthase," Plant J., 3: 763-772 (1993); genes for molecules such as tannins, suberins, or dyes that might confer valuable color to fibers (Ryser, "Cotton Fiber Initiation and Histodifferentiation," In: A. S. Basra (ed.), Cotton Fibers: Developmental Biology. Quality Improvement, and Textile Processing, The Haworth Press, New York, pp. 1-46 (1999); genes for molecules such as cutin, suberin, or wax that might change the absorptivity and strength of cotton fibers (May, "Genetic Variation in Fiber Quality," In: A. S. Basra (ed.), Cotton Fibers: Developmental Biology, Quality Improvement, and Textile Processing, The Haworth Press, New York, pp. 183-230 (1999); Ryser, "Cotton Fiber Initiation and Histodifferentiation," In: A. S. Basra (ed.), Cotton Fibers: Developmental Biology. Quality Improvement, and Textile Processing, The Haworth Press, New York, pp. 1-46 (1999); and genes for signal transduction molecules such as Rac that may regulate shifts between fiber developmental stages (Delmer et al., "Genes Encoding Small GTP-Binding Proteins Analogous to Mammalian rac are Preferentially Expressed in Developing Cotton Fibers," Mol. Gen. Genet., 248: 43-51 (1995).

Particularly preferred protein encoding regions are N-acetylglucosamine synthase coding regions as described e.g. in WO2006/136351 or sucrose synthase genes as described in WO2002/45485 or EP06015433.3 (herein incorporated by reference).

Biologically active RNA may also code for so-called antisense RNA, sense RNA, double stranded RNA as described in WO99/53053 or synthetic micro RNA molecules designed, according to rules well known in the art, to downregulate the expression of other genes comprised within the cell of the fiber-producing plants or even of genes comprised within a pathogen or pest feeding upon the fiber producing plant.

Also provided are methods to express a protein or biologically active RNA specifically in fiber cells of a fiber producing plant, comprising the step of introducing a DNA molecule comprising a fiber selective promoter or promoter region as herein described operably linked to a transcribed DNA region encoding the biologically active RNA molecule, into the fiber cells of a fiber producing plants.

In the second aspect of the current invention, a method is provided for altering the fiber length of a fiber in a fiber producing plant by specifically altering the expression of one of the subgenomic alleles encoding a fiber selective β-1,3-endoglucanase. As indicated above, such alteration of the expression may prevent or enhance degradation of the callose plugging the plasmodesmata at the base of the fiber cell, and thus increase or decrease the rapid fiber elongation phase and the fiber length e.g. in cotton, particularly in *Gossypium hirsutum*. Modulation of the length of the fiber may also impact strength and other qualities or properties of the fiber. Accordingly, the invention is also directed at altering fiber properties or qualities of the fiber by the herein described methods.

In one embodiment of the second aspect of the invention, a method is provided for increasing the length of a fiber in a cotton plant, particularly a *Gossypium hirsutum* plant, by introducing a chimeric gene into cells of said cotton plant whereby the chimeric gene comprises the following operably linked DNA elements:
  a. a plant expressible promoter
  b. a transcribed DNA region which when transcribed yields a biologically active RNA molecule capable of reducing the expression of reducing the expression of a fiber selective β-1,3 endoglucanase comprised within the D genome and
  c. a 3' end region comprising transcription termination and polyadenylation signals functioning in cells of said plant, As has been uncovered by the current inventors, the increased expression of β-1,3 endoglucanase in the fiber cells of a cotton plant previously reported to be correlated with the reopening of the plasmodesmata and marking the end of the rapid fiber elongation phase, is specifically due to the onset of the expression of the D subgenome specific allele at this time, while the A subgenome specific allele is only expressed at later stages in the fiber development, at least in *Gossypium hirsutum*. Accordingly, the methods as described in WO 2005/017157 can be further improved, at least for *Gossypium hirsutum* by specifically altering the expression pattern of a particular subgenomic allele encoding the fiber selective β-1,3 endoglucanase.

As described herein, a D subgenome specific allele encoding a fiber selective β-1,3 endoglucanase can be recognized in several manners. Isolation of the (genomic) nucleic acid encoding a fiber selective β-1,3 endoglucanase from the D subgenome of different cotton plants, as well as from diploid cotton progenitor plants with a D like genome revealed that the intron in the A-subgenomic allele had an about 18 nt long insertion in the intron sequence (see FIG. 3) which is absent in the intron sequence of the D-subgenomic allele.

Furthermore, comparison of the nucleotide sequences of the coding region (cDNA; FIG. 2) and encoded amino acid sequences (FIG. 4) revealed a number of characteristic differences between A and D-subgenomic alleles and encoded proteins, indicated in the figures by the gray boxes.

Very conveniently, the A and D subgenomic alleles can be distinguished by a polymorphism resulting in the presence of an AlwI restriction enzyme recognition site about 326 nucleotides downstream the translation initiation codon in the genomic clone of the A subgenomic allele, which is absent in D subgenomic alleles encoding the fiber selective β-1,3 endoglucanase. One possible method to distinguish A and D subgenomic alleles, both on genomic DNA or cDNA level, is PCR amplification using cDNA or genomic DNA as template and the oligonucleotides having the nucleotide sequence of SEQ ID No 5 and 6 as primers, followed by a digestion of the amplified PCR product with AlwI restriction enzyme. The PCR generated product which is about 656 bp for both subgenomic alleles is cleaved into a 538 and 118 bp fragment when the PCR product is generated from a D-subgenomic allele template, while the PCR generated product amplified from the A-subgenomic allele template is cleaved into three fragments of 476 bp, 118 bp and 59 bp respectively. The presence of the 118 bp serves as an internal control for proper functioning of the restriction enzyme reaction.

Several methods are available in the art to produce a silencing RNA molecule, i.e. an RNA molecule which when expressed reduces the expression of a particular gene or group of genes, including the so-called "sense" or "antisense" RNA technologies.

Thus in one embodiment, the inhibitory RNA molecule encoding chimeric gene is based on the so-called antisense technology. In other words, the coding region of the chimeric gene comprises a nucleotide sequence of at least 19 or 20 consecutive nucleotides of the complement of the nucleotide sequence of the fiber selective β-1,3 endoglucanase. Such a chimeric gene may be constructed by operably linking a DNA fragment comprising at least 19 or 20 nucleotides from fiber selective β-1,3 endoglucanase encoding gene, isolated or identified as described elsewhere in this application, in inverse orientation to a plant expressible promoter and 3' end formation region involved in transcription termination and polyadenylation.

In another embodiment, the inhibitory RNA molecule encoding chimeric gene is based on the so-called co-suppression technology. In other words, the coding region of the chimeric gene comprises a nucleotide sequence of at least 19 or 20 consecutive nucleotides of the nucleotide sequence of the fiber selective β-1,3 endoglucanase gene. Such a chimeric gene may be constructed by operably linking a DNA fragment comprising at least 19 or 20 nucleotides from the fiber selective β-1,3 endoglucanase gene, in direct orientation to a plant expressible promoter and 3' end formation region involved in transcription termination and polyadenylation.

The efficiency of the above mentioned chimeric genes in reducing the expression of the fiber selective β-1,3 endoglucanase gene may be further enhanced by the inclusion of DNA element which result in the expression of aberrant, unpolyadenylated inhibitory RNA molecules or results in the retention of the inhibitory RNA molecules in the nucleus of the cells. One such DNA element suitable for that purpose is a DNA region encoding a self-splicing ribozyme, as described in WO 00/01133 (incorporated by reference). Another such DNA element suitable for that purpose is a DNA region encoding an RNA nuclear localization or retention signal, as described in PCT/AU03/00292 published as WO03/076619 (incorporated by reference).

A convenient and very efficient way of downregulating the expression of a gene of interest uses so-called double-stranded RNA (dsRNA) or interfering RNA (RNAi), as described e.g. in WO99/53050 (incorporated by reference). In this technology, an RNA molecule is introduced into a plant cell, whereby the RNA molecule is capable of forming a double stranded RNA region over at least about 19 to about 21 nucleotides, and whereby one of the strands of this double stranded RNA region is about identical in nucleotide sequence to the target gene ("sense region"), whereas the other strand is about identical in nucleotide sequence to the complement of the target gene or of the sense region ("antisense region"). It is expected that for silencing of the target gene expression, the nucleotide sequence of the 19 consecutive nucleotide sequences may have one mismatch, or the sense and antisense region may differ in one nucleotide. To achieve the construction of such RNA molecules or the encoding chimeric genes, use can be made of the vector as described in WO 02/059294.

Thus, in one embodiment of the invention, a method for increasing the length of a fiber of a fiber producing plant, such as cotton, is provided comprising the step of introducing a chimeric gene into a cell of the fiber producing plant, wherein the chimeric gene comprises the following operably linked DNA elements:

(a) a plant expressible promoter, preferably a plant expressible promoter which controls transcription preferentially in the fiber cells;
(b) a transcribed DNA region, which when transcribed yields a double-stranded RNA molecule capable of reducing specifically the expression of a fiber selective β-1,3 endoglucanase subgenomic allele, and the RNA molecule comprising a first and second RNA region wherein
  i) the first RNA region comprises a nucleotide sequence of at least 19 consecutive nucleotides having at least about 94% sequence identity to the nucleotide sequence of the subgenomic allele;
  ii) the second RNA region comprises a nucleotide sequence complementary to the at least 19 consecutive nucleotides of the first RNA region;
  iii) the first and second RNA region are capable of base-pairing to form a double stranded RNA molecule between at least the 19 consecutive nucleotides of the first and second region; and
(c) a 3' end region comprising transcription termination and polyadenylation signals functioning in cells of the plant.

The length of the first or second RNA region (sense or antisense region) may vary from about 19 nucleotides (nt) up to a length equaling the length (in nucleotides) of the endogenous gene involved in callose removal. The total length of the sense or antisense nucleotide sequence may thus be at least at least 25 nt, or at least about 50 nt, or at least about 100 nt, or at least about 150 nt, or at least about 200 nt, or at least about 500 nt. It is expected that there is no upper limit to the total length of the sense or the antisense nucleotide sequence. However for practical reasons (such as e.g. stability of the chimeric genes) it is expected that the length of the sense or antisense nucleotide sequence should not exceed 5000 nt, particularly should not exceed 2500 nt and could be limited to about 1000 nt.

It will be appreciated that the longer the total length of the sense or antisense region, the less stringent the requirements for sequence identity between these regions and the corresponding sequence in the fiber selective β-1,3 endoglucanase gene or its complement. Preferably, the nucleic acid of interest should have a sequence identity of at least about 75% with the corresponding target sequence, particularly at least about 80%, more particularly at least about 85%, quite particularly about 90%, especially about 95%, more especially about 100%, quite especially be identical to the corresponding part of the target sequence or its complement. However, it is preferred that the nucleic acid of interest always includes a sequence of about 19 consecutive nucleotides, particularly about 25 nt, more particularly about 50 nt, especially about 100 nt, quite especially about 150 nt with 100% sequence identity to the corresponding part of the target nucleic acid. Preferably, for calculating the sequence identity and designing the corresponding sense or antisense sequence, the number of gaps should be minimized, particularly for the shorter sense sequences.

dsRNA encoding chimeric genes according to the invention may comprise an intron, such as a heterologous intron, located e.g. in the spacer sequence between the sense and antisense RNA regions in accordance with the disclosure of WO 99/53050 (incorporated herein by reference).

It is preferred for the current invention that the target specific gene sequence included in the antisense, sense or double stranded RNA molecule comprises at least one nucleotide, and preferably more which are specific for the subgenomic allele whose expression is to be downregulated. Such specific nucleotides are indicated at least in FIG. 2 by the gray boxes.

In a preferred embodiment, the biologically active RNA is specifically adapted to downregulate the D-subgenomic allele of the fiber selective β-1,3 endoglucanase encoding gene (GhGluc1). In another preferred embodiment, the biologically active RNA is specifically adapted to downregulate the A-subgenomic allele of the fiber selective β-1,3 endoglucanase encoding gene (GhGluc1).

The use of synthetic micro-RNAs to downregulate expression of a particular gene in a plant cell, provides for very high sequence specificity of the target gene, and thus allows conveniently to discriminate between closely related alleles as target genes the expression of which is to be downregulated.

Thus, in another embodiment of the invention, the biologically active RNA or silencing RNA or inhibitory RNA molecule may be a microRNA molecule, designed, synthesized and/or modulated to target and cause the cleavage of specific subgenomic alleles, preferably the D-subgenomic allele of fiber selective β-1,3 endoglucanase encoding gene in a fiber producing plants, such as a cotton plant. Various methods have been described to generate and use miRNAs for a specific target gene (including but not limited to Schwab et al. (2006, Plant Cell, 18(5):1121-1133), WO2006/044322, WO2005/047505, EP 06009836, incorporated by reference). Usually, an existing miRNA scaffold is modified in the target gene recognizing portion so that the generated miRNA now guides the RISC complex to cleave the RNA molecules transcribed from the target nucleic acid. miRNA scaffolds could be modified or synthesized such that the miRNA now comprises 21 consecutive nucleotides of one of the subgenomic alleles of the fiber selective β-1,3 endoglucanase encoding nucleotide sequence, such as the sequences represented in the Sequence listing, and allowing mismatches according to the herein below described rules.

Thus, in one embodiment, the invention provides a method for downregulating the expression of a or increasing the resistance of plants to adverse growing conditions, comprising the steps of
  a. Introducing a chimeric gene into cells of said plants, said chimeric gene comprising the following operably linked DNA regions:
    i. A plant expressible promoter;
    ii. A DNA region which upon introduction and transcription in a plant cell is processed into a miRNA, whereby the miRNA is capable of recognizing and guiding the cleavage of the mRNA of one subgenomic allele of a fiber selective β-1,3 endoglucanase encoding gene of the plant but not the other subgenomic allele; and
    iii. optionally, a 3' DNA region involved in transcription termination and polyadenylation.

The mentioned DNA region processed into a miRNA may comprise a nucleotide sequence which is essentially complementary to a nucleotide sequence of at least 21 consecutive nucleotides of a fiber selective β-1,3 endoglucanase encoding gene, provided that one or more of following mismatches are allowed:
  a. A mismatch between the nucleotide at the 5' end of the miRNA and the corresponding nucleotide sequence in the RNA molecule;
  b. A mismatch between any one of the nucleotides in position 1 to position 9 of the miRNA and the corresponding nucleotide sequence in the RNA molecule;
  c. Three mismatches between any one of the nucleotides in position 12 to position 21 of the miRNA and the corresponding nucleotide sequence in the RNA molecule provided that there are no more than two consecutive mismatches.

As used herein, a "miRNA" is an RNA molecule of about 20 to 22 nucleotides in length which can be loaded into a RISC complex and direct the cleavage of another RNA molecule, wherein the other RNA molecule comprises a nucleotide sequence essentially complementary to the nucleotide sequence of the miRNA molecule whereby one or more of the following mismatches may occur:
  a. A mismatch between the nucleotide at the 5' end of said miRNA and the corresponding nucleotide sequence in the target RNA molecule;
  b. A mismatch between any one of the nucleotides in position 1 to position 9 of said miRNA and the corresponding nucleotide sequence in the target RNA molecule;
  c. Three mismatches between any one of the nucleotides in position 12 to position 21 of said miRNA and the corresponding nucleotide sequence in the target RNA molecule provided that there are no more than two consecutive mismatches.
  d. No mismatch is allowed at positions 10 and 11 of the miRNA (all miRNA positions are indicated starting from the 5' end of the miRNA molecule).

A miRNA is processed from a "pre-miRNA" molecule by proteins, such as DCL proteins, present in any plant cell and loaded onto a RISC complex where it can guide the cleavage of the target RNA molecules.

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop and further comprising the nucleotide sequence of the miRNA (and its complement sequence) in the double stranded RNA stem. Preferably, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. An example of a synthetic pre-miRNA is represented in FIG. 1. Preferably, the difference in free energy between unpaired and paired RNA structure is between −20 and −60 kcal/mole, particularly around −40 kcal/mole. The complementarity between the miRNA and the miRNA* need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

The pre-miRNA molecules (and consequently also the miRNA molecules) can be conveniently introduced into a plant cell by providing the plant cells with a gene comprising a plant-expressible promoter operably linked to a DNA region, which when transcribed yields the pre-miRNA molecule. The plant expressible promoter may be the promoter naturally associated with the pre-miRNA molecule or it may be a heterologous promoter.

Suitable miRNA and pre microRNA molecules for the specific downregulation of the expression of the D-subgenomic allele of GhGluc1 gene are set forth in the sequence listing entries SEQ ID No 15, 16, 20 and 21.

Suitable miRNA and pre microRNA molecules for the specific downregulation of the expression of the A-subgenomic allele of GhGluc1 gene are set forth in the sequence listing entries SEQ ID No 13, 14, 17, 18 and 19.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, or T-DNA gene promoters and the like.

A plant-expressible promoter that controls initiation and maintenance of transcription preferentially in fiber cells is a promoter that drives transcription of the operably linked DNA region to a higher level in fiber cells and the underlying epidermis cells than in other cells or tissues of the plant. Such promoters include the promoter from cotton from a fiber-specific β-tubulin gene (as described in WO0210377), the promoter from cotton from a fiber-specific actin gene (as described in WO0210413), the promoter from a fiber specific lipid transfer protein gene from cotton (as described in U.S. Pat. No. 5,792,933), a promoter from an expansin gene from cotton (WO9830698) or a promoter from a chitinase gene in cotton (US2003106097) or the promoters of the fiber specific genes described in U.S. Pat. No. 6,259,003 or U.S. Pat. No. 6,166,294. Fiber selective promoters as described herein may also be used.

For some applications, it may be beneficial to decrease the fiber length in a fiber producing plant, such as a cotton plant. E.g. it would be beneficial to decrease the amount of fuzz fiber in a cotton plant, thus leaving more energy and material for incorporation into the lint fiber in cotton plants. This may be conveniently achieved by (over)expressing a β-1,3-endoglucanase in fiber cells at an early stage in the development of a fiber cell e.g. using a fiber selective promoter as described herein which is expressed at the end of the rapid elongation phase.

The invention also encompasses the chimeric genes herein described, as well as plants, seeds, tissues comprising these chimeric genes, and fibers produced from such plants Fiber length or other fiber properties and fiber quality in cotton may also be increased or altered by isolating D-subgenome allelic variants which no longer encode a functional β-1,3-endoglucanase or which encode a variant protein with weak enzymatic activity.

Methods to transform plants are well known in the art and are of minor relevance for the current invention. Methods to transform cotton plants are also well known in the art. *Agrobacterium*-mediated transformation of cotton has been described e.g. in U.S. Pat. No. 5,004,863 or in U.S. Pat. No. 6,483,013 and cotton transformation by particle bombardment is reported e.g. in WO 92/15675.

The chimeric genes according to the invention may be introduced into plants in a stable manner or in a transient manner using methods well known in the art. The chimeric genes may be introduced into plants, or may be generated inside the plant cell as described e.g. in EP 1339859.

The chimeric genes may be introduced by transformation in cotton plants from which embryogenic callus can be derived, such as Coker 312, Coker310, Coker 5Acala SJ-5, GSC25110, FIBERMAX 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 ORO BLANCO PIMA, FIBERMAX FM5013, FIBERMAX FM5015, FIBERMAX FM5017, FIBERMAX FM989, FIBERMAX FM832, FIBERMAX FM966, FIBERMAX FM958, FIBERMAX FM989, FIBERMAX FM958, FIBERMAX FM832, FIBERMAX FM991, FIBERMAX FM819, FIBERMAX FM800, FIBERMAX FM960, FIBERMAX FM966, FIBERMAX FM981, FIBERMAX FM5035, FIBERMAX FM5044, FIBERMAX FM5045, FIBERMAX FM5013, FIBERMAX FM5015, FIBERMAX FM5017 or FIBERMAX FM5024 and plants with genotypes derived thereof.

"Cotton" as used herein includes *Gossypium hirsutum* or *Gossypium barbadense*. "Cotton progenitor plants" include *Gossypium arboreturn*, *Gossypium herbaceum* and *Gossypium raimondii* and *Gossypium longicalyx*.

The methods and means of the current invention may also be employed for other plant species such as hemp, jute, flax and woody plants, including but not limited to *Pinus* spp., *Populus* spp., *Picea* spp., *Eucalyptus* spp. etc.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

In another embodiment of the invention, antibodies raised against the β-1,3-endoglucanase are provided, particularly antibodies recognizing the β-1,3-endoglucanase proteins having the amino acid sequences of SEQ ID Nos. 11 and 12.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The following non-limiting Examples describe the identification of two β-1,3-endoglucanases of the A and D subtype in cotton as well as their promoter regions, and analysis of the timing of expression and involvement in secondary plant cell wall synthesis. Also described are chimeric genes for the alteration of fiber characteristics, for fiber-preferential and for fiber-specific expression in fiber-producing plants such as cotton and uses thereof. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and Examples, reference is made to the following sequences represented in the sequence listing:

SEQ ID No 1: amplified genomic fragment of β-1,3-endoglucanase from *Gossypium hirsutum* Fiber Max966, subtype A SEQ ID No 2: amplified genomic fragment of β-1,3-endoglucanase from *Gossypium hirsutum* Fiber Max966, subtype D SEQ ID No 3: amplified genomic fragment of β-1,3-endoglucanase from *Gossypium arboreturn*

SEQ ID No 4: amplified genomic fragment of β-1,3-endoglucanase from *Gossypium raimondii*

SEQ ID No 5: reverse primer (SE002) for amplification of β-1,3-endoglucanase genomic fragment SEQ ID No 6: forward primer (SE003) for amplification of β-1,3-endoglucanase genomic fragment SEQ ID No 7: amino acid sequence encoded by the amplified genomic fragment of β-1,3-endoglucanase from *Gossypium hirsutum* Fiber Max966, subtype A SEQ ID No 8: amino acid sequence encoded by the amplified genomic fragment of β-1,3-endoglucanase from *Gossypium hirsutum* Fiber Max966, subtype D SEQ ID No 9: nucleotide sequence of the complete genomic clone of β-1,3-endoglucanase from *Gossypium hirsutum* Fiber Max966, subtype A, including promoter sequence SEQ ID No 10: nucleotide sequence of the complete genomic clone of β-1,3-endoglucanase from *Gossypium hirsutum* Fiber Max966, subtype D, including promoter sequence SEQ ID No 11: amino acid sequence of complete β-1,3-endoglucanase from *Gossypium hirsutum* Fiber Max966, subtype A SEQ ID No 12: amino acid sequence of complete β-1,3-endoglucanase from *Gossypium hirsutum* Fiber Max966, subtype D SEQ ID No 13: nucleotide sequence of pre-miRA1

SEQ ID No 14: nucleotide sequence of pre-miRA1 with cloning sites

SEQ ID No 15: nucleotide sequence of pre-miRD1

SEQ ID No 16: nucleotide sequence of pre-miRD1 with cloning sites

SEQ ID No 17: nucleotide sequence of pre-miRA2

SEQ ID No 18: nucleotide sequence of pre-miRA2aa

SEQ ID No 19: nucleotide sequence of pre-miRA2aa with cloning sites

SEQ ID No 20: nucleotide sequence of pre-miRD2

SEQ ID No 21: nucleotide sequence of pre-miRD2 with cloning sites

EXAMPLE 1

Identification of a and D-Subgenome Specific Alleles Encoding a Fiber Selective β-1,3-Glucanase in Cotton Plants and Cotton Progenitor Plants It has been proposed that callose is involved in the process of maintaining turgor in growing fiber cells. The removal of callose at the base of bridging structures between fiber and non-fiber cotton cells, known as plasmadesmata, dissipates the turgor pressure. This results in the termination of rapid fiber elongation. Therefore by delaying the removal of callose fiber length should be enhanced.

The β-1,3-glucanase enzyme catalyzes the hydrolysis of β-1,3-D-glucosidic linkages in β-1,3-D-glucan (callose). A fiber specific β-1,3-glucanase gene encoded by GhGluc1, was undetectable when callose was deposited at the fiber base but became evident at the time of callose degradation.

In short, plasmodesmata closure appears to play an important role in elongating cotton fibers. Callose deposition and degradation should be involved in the plasmodesmata closure and reopening, respectively. The expression of GhGluc1 could play a role in this process by degrading callose, thus opening the plasmodesmata. (Ruan et al., 2004, Plant Physiology—136: 4104-4113).

Based on the GhGluc1 nucleotide sequence (EMBL accession number D88416) described in Ruan et al., 2004, Plant Physiology—136: 4104-4113, 2 primers (SE002: ggccgaagccgatcttatctagg (reverse primer; SEQ ID No 5) en SE003: cggcaacaatcttccatctccag (forward primer, SEQ ID No 6)) were designed to amplify genomic DNA fragments for *G. hirsutum* (AD genome), *G. arboreum* (A genome) and *G. raimondii* (D genome). These fragments have been sequenced (see SEQ ID No 1-4). For *G. hirsutum* 2 consensus sequences were derived, for *G. arboreum* 1 consensus sequence was derived and for *G. raimondii* 1 consensus sequence was derived.

Overview of polymorphisms between the two *G. hirsutum* sequences and the two diploid sequences:

| ID | taxon | genome | 75 | 120 | 135 | 167 | 170 | 174 | 201 | 202 | 256 | 265 | 270 | 271 | 274 | 279 | 280 | 299 | 307 | 327 | 355 | 360 | 368 | 376 |
|---|---|---|---|---|---|---|---|---|---|---|---|---|---|---|---|---|---|---|---|---|---|---|---|---|
| GaGluc1 | *G. arboreum* | A | A | – | G | A | A | C | C | G | C | A | G | G | C | T | C | C | G | G | C | C | C | G |
| GhGluc1-SGA | *G. hirsutum* | AD | T | C | C | A | A | C | C | G | A | A | G | G | C | T | C | C | G | G | G | C | C | G |
| GhGluc1-SGD | *G. hirsutum* | AD | A | C | C | G | C | G | A | A | C | G | A | G | G | C | T | T | A | A | C | T | T | G |
| GrGluc1 | *G. raimondii* | D | A | C | C | G | C | G | A | A | C | G | A | A | G | C | T | T | A | A | C | C | T | A |

| ID | taxon | genome | 492 | 494 | 495 | 569 | 571 |
|---|---|---|---|---|---|---|---|
| GaGluc1 | *G. arboreum* | A | T | C | G | A | C |
| GhGluc1-SGA | *G. hirsutum* | AD | T | C | G | A | C |
| GhGluc1-SGD | *G. hirsutum* | AD | C | G | T | G | T |
| GrGluc1 | *G. raimondii* | D | C | G | T | G | T |

Accordingly, one type of the sequence corresponds to the A genome sequence, and the other type corresponds to the D genome.

Using an AlwI (recognition site=GGATC) digest on the amplified PCR fragment, both subgenomic variants within the hirsutum or genome can be distinguished (see FIG. 5.) Thus the following protocol can be used to distinguish A and D subgenome alleles of GhGluc1. The primers used are:

a. SE002: GGCCGAAGCCGATCTTATCTAGG     (SEQ ID No 5)

b. SE003: CGGCAACAATCTTCCATCTCCAG     (SEQ ID No 6)

The expected length PCR product is 655 bp.
PCR Conditions:

|  | 1 x |
| --- | --- |
| Template DNA (200 ng/µl) | 1 µl |
| 5 × GreenGoTaq buffer | 5 µl |
| SE002 (10 µM) | 0.75 µl |
| SE003 (10 µM) | 0.75 µl |
| dNTP's (20 mM) | 0.5 µl |
| GoTaq polymerase | 0.25 µl |
| MQ water | 16.75 µl |
|  | 25 µl |

| PCR profile |
| --- |
| 95° C. - 5 min |
| 95° C. - 1 min ⎫ |
| 58° C. - 1 min ⎬ 5 x |
| 72° C. - 2 min ⎭ |
| 93° C. - 30 s ⎫ |
| 58° C. - 30 s ⎬ 25 x |
| 72° C. - 1 min ⎭ |
| 72° C. - 10 min |

After PCR amplification, the PCR fragment is digested with AlwI digest (3 h incubation @ 37° C.) using 10 µl template; 1 µl AlwI enzyme; 2 µl NEB 4 restriction buffer; 7 µl MQ water. The resulting fragments are analysed on 1.5% TAE gel stained with EtBr.

The expected band sizes for the A subgenome allele specific PCR fragment are: 479+118+59 bp. The expected band sizes for the D subgenome allele specific PCR fragment are: 538+118 bp.

EXAMPLE 2

Differential Expression of A and D-Subgenome Specific Alleles Encoding a Fiber Selective β-1,3-Glucanase and Correlation with Fiber Development Stages in *Gossypium hirsutum*

Allelic specific expression across fiber growth/developmental profile was analyzed for *G. hirsutum*. DNA from the cDNA libraries created from fiber cells and seed at 5DPA and from fiber cells at 10, 15, 20 and 40 DPA was extracted, the concentration was equalized and the above mentioned PCR amplification was performed. Differences in band intensities correspond to relative differences in expression (FIG. 6, lanes 2, 4, 6, 8 and 10. A positive control (genomic DNA) was included (FIG. 6, lane 12). An AlwI digest was performed as described in Example 1 to distinguish between the 2 subgenomic alleles of the GhGluc1 genes in (FIG. 6, lanes 3, 5, 7, 9, 11 and 13).

The expression profile can be summarized as follows:

| 5 dpa | 10 dpa | 15 dpa | 20 dpa | 30 dpa | 40 dpa |
| --- | --- | --- | --- | --- | --- |
| / | / | D | D | A and D | A and D |

During the rapid elongation phase in fiber development (5 and 10 dpa), there is no expression of GhGluc1. Therefore, the callose plug is not degraded; the turgor in the cell is not released and elongation continues. We believe that the faint band at 5 dpa indicates some expression in the seed (not in the fiber). At the transition between the elongation phase and secondary cell wall formation phase (15 DPA), GhGluc1 is expressed. This releases the turgor in the cell in rapid elongation stops. Only the D genome like variant of the GhGluc1 gene in is expressed. At 20 DPA there is more expression then at 15 DPA (more intense band). The A genome like variant is not expressed at 15 and 20 DPA. The A genome like variant, as well as the D genome like variant, is expressed at 30 and 40 DPA and might play a role in maturation or other fiber properties.

EXAMPLE 3

Isolation and Identification of Promoter Region of A and D-Subgenome Specific Alleles Encoding a Fiber Selective β-1,3-Glucanase PCR fragment comprising the nucleotide sequence of the A and D subgenomic specific alleles of GhGluc1 were used to screen a BAC library containing genomic DNA clones of *Gossypium hirsutum* variety. 4 different clones were identified, 2 for each subgenomic variant. The nucleotide sequence of genomic fragments for each of the allelic variants were identified and are represented in SEQ ID no 9 (A genome) and SEQ ID No 10 (D genome).

For the A-genome variant, a TATA box could be identified at positions 2278 to 2281; a transcription initiation site at position 2308. The 5' untranslated leader extends from nucleotide 2308 to 2409; the translation initiation codon is located at positions 2410 to 2412. The coding sequence consist of two exons (nt 2410 to 2443 and nt 2556 to 3499) separated by an intron sequence (2444 to 2555). The translation stop codon is located at position 3497 to 3499 and the polyadenylation site is located at position 3624.

For the D-genome variant, a TATA box could be identified at positions 3242 to 3245; a transcription initiation site at position 3270. The 5' untranslated leader extends from nucleotide 3270 to 3372; the translation initiation codon is located at positions 3373 to 3375. The coding sequence consist of two exons (nt 3373 to 3406 and nt 3501 to 4444) separated by an intron sequence (nt 3407 to 3500). The translation stop codon is located at position 4442 to 4444 and the polyadenylation site is located at position 4566.

The nucleotide sequence of the fused coding regions has been aligned (FIG. 2), and differences are indicated; similarly the nucleotide sequences of the introns have been aligned (FIG. 3). FIG. 4 shows an alignment of the encoded proteins, while FIG. 1 shows an alignment of the nucleotide sequences located upstream of the coding region.

EXAMPLE 4

Chimeric Gene Constructs Comprising Different Fiber Selective Promoter Regions Operably Linked to a Marker Gene The following DNA fragments were operably linked using standard recombinant techniques:

a. The nucleotide sequence of the A-allele specific promoter comprising the nucleotide sequence of SEQ ID No 9 from nucleotide 465 to nucleotide 2409 (indicated hereinafter as Gluc1-SGA (A1.9) has been deposited under accession number LMBP 8351)

b. A β-glucuronidase coding region (GUS)

c. A fragment comprising a transcription termination and polyadenylation signal (CaMV) 3' 35S and d. The nucleotide sequence of the A-allele specific promoter comprising the nucleotide sequence of SEQ ID No 9 from nucleotide 1374 to nucleotide 2409.

e. A β-glucuronidase coding region (GUS)

f. A fragment comprising a transcription termination and polyadenylation signal (CaMV) 3' 35S and g. The nucleotide sequence of the A-allele specific promoter comprising the nucleotide sequence of SEQ ID No 9 from nucleotide 1531 to nucleotide 2409.

h. A β-glucuronidase coding region (GUS)

i. A fragment comprising a transcription termination and polyadenylation signal (CaMV) 3' 35S and j. The nucleotide sequence of the D-allele specific promoter comprising the nucleotide sequence of SEQ ID No 10 from nucleotide 1397 to nucleotide 3372. (indicated hereinafter as Gluc1-SGD (D2.0))

k. A β-glucuronidase coding region (GUS)

l. A fragment comprising a transcription termination and polyadenylation signal (CaMV) 3' 35S And m. The nucleotide sequence of the D-allele specific promoter comprising the nucleotide sequence of SEQ ID No 10 from nucleotide 2371 to nucleotide 3372.

n. A β-glucuronidase coding region (GUS)

o. A fragment comprising a transcription termination and polyadenylation signal (CaMV) 3' 35S Or p. The nucleotide sequence of the D-allele specific promoter comprising the nucleotide sequence of SEQ ID No 10 from nucleotide 2718 to nucleotide 3372.

q. A β-glucuronidase coding region (GUS)

r. A fragment comprising a transcription termination and polyadenylation signal (CaMV) 3' 35S.

The above chimeric genes were separately cloned into a T-DNA vector, in the presence of a chimeric selectable marker gene, and introduced into *Agrobacterium tumefaciens* strain comprising a disarmed helper Ti-plasmid. The *Agrobacterium* strains were used to generate transgenic cotton plants according to the method described in WO00/71733. Fiber cells and other tissue from these plants are histochemically stained.

Expression of the different chimeric constructs is predominantly observed in fiber cells and fibers.

EXAMPLE 5

Chimeric Gene Constructs Comprising Different Fiber Selective Promoter Regions Operably Linked to N-Acetylglucosamine Transferase Coding Region Constructs similar to the constructs of Example 4, but wherein the Gus coding region has been exchanged for a NodC coding region (see WO2006/136531, specifically SEQ ID 1 to 9 therein, incorporated by reference) preceded by a Cab22 untranslated leader sequence, were assembled using current recombinant DNA techniques.

These chimeric genes are separately cloned into a T-DNA vector, in the presence of a chimeric selectable marker gene, and introduced into *Agrobacterium tumefaciens* strain comprising a disarmed helper Ti-plasmid. The *Agrobacterium* strains are used to generate transgenic cotton plants according to the method described in WO00/71733. Fiber cells and other tissue from these plants are analyzed for the presence of positively charged oligosaccharides as described in WO2006/136531).

EXAMPLE 6

Increasing Fiber Length in *Gossypium hirsutum* by Downregulating Specifically the D-Subgenome Specific Alleles Encoding a Fiber Selective β-1,3-Glucanase Synthetic pre-microRNAs specific for either the A or the D subgenomic allelic variant of GhGluc1 have been designed using design rules available in the art.

Suitable miRNA and pre microRNA molecules for the specific downregulation of the expression of the D-subgenomic allele of GhGluc1 gene are set forth in the sequence listing entries SEQ ID No 15, 16, 20 and 21.

Suitable miRNA and pre microRNA molecules for the specific downregulation of the expression of the A-subgenomic allele of GhGluc1 gene are set forth in the sequence listing entries SEQ ID No 13, 14, 17, 18 and 19.

The premicroRNA encoding nucleotide sequences are cloned under control of a CaMV 35S promoter or under control of a fiber-specific and/or fiber-preferential promoter as described in Example 4.

These chimeric genes are separately cloned into a T-DNA vector, in the presence of a chimeric selectable marker gene, and introduced into *Agrobacterium tumefaciens* strain comprising a disarmed helper Ti-plasmid. The *Agrobacterium* strains are used to generate transgenic cotton plants according to the method described in WO00/71733. Fibers from such plants or their progeny are analyzed for increased fiber length.

EXAMPLE 7

Analysis of the Specificity of gluc1 Promoters for Fibers

Figure 7:
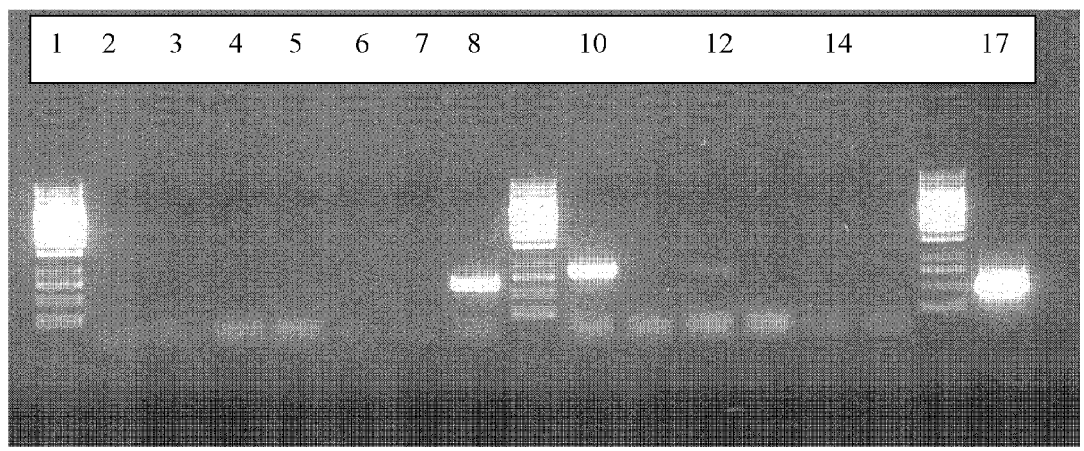
FIG. 7: Expression analysis of GhGluc1 in cotton leaves, roots and stems by RT-PCR. RNA extracted from cotton leaves, roots and stems was subjected to RT-PCR analysis to detect expression of glucanase 1 or protein phosphatase 2A (pp 2A). First strand cDNA synthesis was performed using SuperScript First-Strand Synthesis System from Invitrogen. Lane 1:100 bp ladder; lane 2: cotton leaf RNA sample+Gluc1 specific primers+reverse transcriptase; lane 3: cotton leaf RNA sample+Gluc1 specific primers−reverse transcriptase; lane 4: cotton root RNA sample+Gluc1 specific primers+reverse transcriptase; lane 5: cotton root RNA sample+Gluc1 specific primers−reverse transcriptase; lane 6: cotton stem RNA sample+Gluc1 specific primers+reverse transcriptase; lane 7: cotton stem RNA sample+Gluc1 specific primers−reverse transcriptase; lane 8: genomic DNA (Fibermax 400 ng)+Gluc1 specific primers; lane 9: 100 bp ladder; lane 10: cotton leaf RNA sample+pp 2A specific primers+reverse transcriptase; lane 11: cotton leaf RNA sample+pp 2A specific primers–reverse transcriptase; lane 12: cotton root RNA sample+pp 2A specific primers+reverse transcriptase; lane 13: cotton root RNA sample+pp 2A specific primers–reverse transcriptase; lane 14: cotton stem RNA sample+pp 2A specific primers+reverse transcriptase; lane 15: cotton stem RNA sample+pp 2A specific primers–reverse transcriptase; lane 16: 100 bp ladder; lane 17: positive control RNA (supplied with kit).

RNA was isolated from cotton leaves, roots and stems and analyzed for the expression of gluc1 genes and for the protein phosphatase 2A gene (a ubiquitous and conserved Serine/Threonine phosphatase with broad substrate specificity and diverse cellular functions). First strand cDNA synthesis was performed using the SuperScript First Strand Synthesis system for RT-PCR (Invitrogen), after which the gluc1 or pp 2A specific primers were added and the RT-PCR reaction performed. The results are visualized in FIG. 7. The positive result in lane 17 indicated that first strand synthesis was successfully achieved. Positive results in lanes 10, 12, 14 using pp 2A specific primers in leaf, root and stem RNA samples specifically indicated that first strand synthesis in leaf, root and stem sample worked. Lanes 11, 13, 15 are negative controls omitting the reverse transcriptase from the reaction. Lane 8 is a positive control consisting of genomic DNA to verify the correctness of the gluc1 specific PCR reaction. In lanes 2, 4, 6 no signal can be detected indicating the absence of Gluc1 expression in cotton leaves, roots and stems. Lanes 3, 5 and 7 are negative controls omitting the reverse transcriptase.

In conclusion, no Gluc1 expression could be detected in cotton leaf, root and stem tissue.

EXAMPLE 8

Cotton Ovule Transformation with *Agrobacterium* Strains Containing the

Ovules of cotton flowers were isolated at 0DPA, 1DPA and 2DPA and used for ovule culture experiments (as described e.g. by Feng and Brown, 2000, In vitro Cellular & Developmental Biology, Volume 36, Number 4 pages 293-299) after transformation with *Agrobacterium tumefaciens* carrying the different chimeric gluc1 promoter::GUS fusion genes indicated in Example 4 as Gluc1-SGA (A1.9) and Gluc1-SGD (D2.0). The initiating fibers cells/fibers were analyzed histochemically for GUS expression after 1 week, 2 weeks, 3 weeks, 4 weeks or 5 weeks. As a positive control, cultured ovules were included which had been infected with an *Agrobacterium* strain harboring a chimeric CaMV35 promoter::Gus fusion gene. Note that the GUS coding region used contained an intron sequence to avoid accidental GUS expression in the infecting Agrobacteria. The results are summarized in Table 1.

TABLE 1

| Gus histochemical analysis of the cultured and transfected cotton ovules | | | | | |
|---|---|---|---|---|---|
|  | 7DPA | 14DPA | 21DPA | 28DPA | 35DPA |
| CaMV35S-gus | + | + | + | + | + |
| Gluc1-SGA-gus | − | − | − | − | + |
| Gluc1-SGD-gus | − | + | + | + | − |

These data corroborate the expression profiles deduced for the promoters from the different subgenomic alleles for GhGluc1 from the data in Example 2.

The invention claimed is:

1. A chimeric gene comprising the following operably linked DNA regions:
   (a) a fiber cell preferential promoter comprising:
      (i) a nucleotide sequence comprising the nucleotide sequence of SEQ ID No 9 from the nucleotide at position 1531 to the nucleotide at position 2307; or
      (ii) the fiber cell preferential promoter Gluc1-SGA(A 1.9) deposited as LMBP8351 in the BCCM/LMPB, Collections of Micro-organisms, LMBP Plasmid Collection, Belgium;
   (b) a heterologous DNA region encoding a biologically active RNA of interest; and
   (c) a transcription termination and polyadenylation signal.

2. The fiber cell preferential promoter according to claim 1 comprising chimeric gene according to claim 1, wherein said fiber cell promoter comprises the nucleotide sequence of SEQ ID No. 9 from position 465 to position 2307.

3. The chimeric gene according to claim 1, wherein said fiber cell promoter comprises the nucleotide sequence of SEQ ID No 9 from position 1374 to position 2307.

4. The chimeric gene according to claim 1, further comprising the nucleotide sequence of SEQ ID 9 from the nucleotide at position 2308 to the nucleotide at position 2409 between said fiber cell preferential promoter and said heterologous DNA.

5. The chimeric gene according to claim 1, wherein said biologically active RNA encodes a protein of interest.

6. The chimeric gene according to claim 5, wherein said heterologous DNA region encodes a molecule selected from a N-acetylglucosamine transferase, a cellulose synthase, a sucrose synthase, a sucrose phosphate synthase, a β-1,3-endoglucanase, xylan synthase (cslF), xyloglucan synthase (cslD), or 1,3-1,4 glucan synthase (cslC).

7. The chimeric gene according to claim 1, wherein said biologically active RNA is a ribozyme, microRNA, or double stranded hairpin RNA.

8. A plant cell comprising the chimeric gene according to claim 1.

9. A plant comprising the chimeric gene according to claim 1.

10. The plant according to claim 9, wherein said plant is a cotton plant.

11. A seed of a plant comprising the chimeric gene according to claim 1.

12. A method for expressing a biologically active RNA in a cell of a plant, said method comprising
   a) providing the cell of said plant with the chimeric gene according to claim 1;
   and
   b) growing said plant.

13. The method according to claim 12, wherein said plant is a cotton plant.

14. The chimeric gene according to claim 1, wherein said biologically active RNA downregulates the expression of an endogenous cotton gene.

15. The chimeric gene according to claim 14, wherein said endogenous cotton gene encodes β-1,3-endoglucanase.

16. The chimeric gene according to claim 1, wherein the fiber cell preferential promoter comprises the nucleotide sequence of SEQ ID NO: 9 from position 1531 to position 2307.

17. The chimeric gene according to claim 1, wherein the fiber cell preferential promoter comprises a fiber cell preferential promoter Gluc1-SGA(A 1.9) deposited as LMBP8351.

* * * * *

SEQUENCE LISTING

```
<160> NUMBER OF SEQ ID NOS: 21

<210> SEQ ID NO 1
<211> LENGTH: 689
<212> TYPE: DNA
<213> ORGANISM: Gossypium hirsutum

<400> SEQUENCE: 1
tggccgtgat attggtgttt gctatggttt gaacggcaac aatcttccat ctccaggaga      60
tgttattaat cttttcaaaa ctagtggcat aaacaatatc aggctctacc agccttaccc     120
tgaagtgctc gaagcagcaa ggggatcggg aatatccctc tcgatgagta cgacaaacga     180
ggacatacaa agcctcgcaa cggatcaaag tgcagccgat gcatgggtta acaccaacat     240
cgtcccttat aaggaagatg ttcaattcag gttcatcatc attgggaatg aagccattcc     300
aggacagtca agctcttaca ttcctggtgc catgaacaac ataatgaact cgctggcctc     360
atttgggcta ggcacgacga aggttacgac cgtggtcccg atgaatgccc taagtacctc     420
gtaccctcct tcagacggcg cttttggaag cgatataaca tcgatcatga ctagtatcat     480
ggccattctg gttcgacagg attcgcccct cctgatcaat gtgtaccctt attttgccta     540
tgcctcagac cccactcata tttccctcaa ctacgccttg ttcacctcga ccgcaccggt     600
ggtggtcgac caaggcttgg aatactacaa cctctttgac ggcatggtcg atgctttcaa     660
tgccgcccta gataagatcg gcttcggcc                                        689

<210> SEQ ID NO 2
<211> LENGTH: 689
<212> TYPE: DNA
<213> ORGANISM: Gossypium hirsutum

<400> SEQUENCE: 2
tggccgtgat attggtgttt gctatggttt gaacggcaac aatcttccat ctccaggaga      60
tgttattaat ctttacaaaa ctagtggcat aaacaatatc aggctctacc agccttaccc     120
```

```
tgaagtgctc gaagcagcaa ggggatcggg aatatccctc tcgatgggtc cgagaaacga      180
ggacatacaa agcctcgcaa aagatcaaag tgcagccgat gcatgggtta acaccaacat      240
cgtcccttat aaggacgatg ttcagttcaa gttgatcact attgggaatg aagccatttc      300
aggacaatca agctcttaca ttcctgatgc catgaacaac ataatgaact cgctcgcctt      360
atttgggtta ggcacgacga aggttacgac cgtggtcccg atgaatgccc taagtacctc      420
gtaccctcct tcagacggcg cttttggaag cgatataaca tcgatcatga ctagtatcat      480
ggccattctg gctgtacagg attcgcccct cctgatcaat gtgtaccctt attttgccta      540
tgcctcagac cccactcata tttccctcga ttacgccttg ttcacctcga ccgcaccggt      600
ggtggtcgac caaggcttgg aatactacaa cctctttgac ggcatggtcg atgctttcaa      660
tgccgcccta gataagatcg gcttcggcc                                        689

<210> SEQ ID NO 3
<211> LENGTH: 655
<212> TYPE: DNA
<213> ORGANISM: Gossypium arboreum

<400> SEQUENCE: 3
cggcaacaat cttccatctc caggagatgt tattaatctt tacaaaacta gtggcataaa       60
caatatcagg ctctaccagc cttacctgaa gtgctcgaag gagcaagggg atcgggaata      120
tccctctcga tgagtacgac aaacgaggac atacaaagcc tcgaacgga tcaaagtgca      180 gccgatgcat gggttaacac caacatcgtc ccttataagg acgatgttca attcaggttc      240
atcatcattg gaatgaagc cattccagga cagtcaagct cttacattcc tggtgccatg      300
aacaacataa tgaactcgct cgcctcattt gggctaggca cgacgaaggt tacgaccgtg      360
gtcccgatga atgccctaag tacctcgtac cctccttcag acggcgcttt tggaagcgat      420
ataacatcga tcatgactag tatcatggcc attctggttc gacaggattc gcccctcctg      480
atcaatgtgt acccttatt tgcctatgcc tcagacccca ctcatatttc cctcaactac      540
gccttgttca cctcgaccgc accggtggtg gtcgaccaag gcttggaata ctacaacctc      600
tttgacggca tggtcgatgc tttcaatgcc gccctagata agatcggctt cggcc           655

<210> SEQ ID NO 4
<211> LENGTH: 656
<212> TYPE: DNA
<213> ORGANISM: Gossypium raimondii

<400> SEQUENCE: 4
cggcaacaat cttccatctc caggagatgt tattaatctt tacaaaacta gtggcataaa       60
caatatcagg ctctaccagc cttaccctga agtgctcgaa gcagcaaggg gatcgggaat      120
atccctctcg atgggtccga aaacgagga catacaaagc ctcgcaaaag atcaaagtgc      180
agccgatgca tgggttaaca ccaacatcgt cccttataag gacgatgttc agttcaaatt      240
gatcactatt gggaatgaag ccatttcagg acaatcaagc tcttacattc ctgatgccat      300
gaacaacata tgaactcgc tcgcctcatt tgggttaggc acaacgaagg ttacgaccgt      360
ggtcccgatg aatgccctaa gtacctcgta ccctccttca gacggcgctt ttggaagcga      420
tataacatcg atcatgacta gtatcatggc cattctggct gtacaggatt cgcccctcct      480
gatcaatgtg tacccttatt ttgcctatgc ctcagacccc actcatattt ccctcgatta      540
cgccttgttc acctcgaccg caccggtggt ggtcgaccaa ggcttggaat actacaacct      600
ctttgacggc atggtcgatg ctttcaatgc cgccctagat aagatcggct tcggcc          656
```

```
<210> SEQ ID NO 5
<211> LENGTH: 23
<212> TYPE: DNA
<213> ORGANISM: Artificial
<220> FEATURE:
<223> OTHER INFORMATION: oligonucleotide primer for amplification of
      endoglucanase genomic fragment

<400> SEQUENCE: 5
ggccgaagcc gatcttatct agg                                                 23

<210> SEQ ID NO 6
<211> LENGTH: 23
<212> TYPE: DNA
<213> ORGANISM: Artificial
<220> FEATURE:
<223> OTHER INFORMATION: oligonucleotide primer for amplification of
      endoglucanase genomic fragment

<400> SEQUENCE: 6
cggcaacaat cttccatctc cag                                                 23

<210> SEQ ID NO 7
<211> LENGTH: 229
<212> TYPE: PRT
<213> ORGANISM: Gossypium hirsutum

<400> SEQUENCE: 7
```

Gly Arg Asp Ile Gly Val Cys Tyr Gly Leu Asn Gly Asn Asn Leu Pro
1               5                   10                  15

Ser Pro Gly Asp Val Ile Asn Leu Phe Lys Thr Ser Gly Ile Asn Asn
                20                  25                  30

Ile Arg Leu Tyr Gln Pro Tyr Pro Glu Val Leu Glu Ala Ala Arg Gly
            35                  40                  45

Ser Gly Ile Ser Leu Ser Met Ser Thr Thr Asn Glu Asp Ile Gln Ser
        50                  55                  60

Leu Ala Thr Asp Gln Ser Ala Ala Asp Ala Trp Val Asn Thr Asn Ile
65                  70                  75                  80

Val Pro Tyr Lys Glu Asp Val Gln Phe Arg Phe Ile Ile Gly Asn
                85                  90                  95

Glu Ala Ile Pro Gly Gln Ser Ser Ser Tyr Ile Pro Gly Ala Met Asn
            100                 105                 110

Asn Ile Met Asn Ser Leu Ala Ser Phe Gly Leu Gly Thr Thr Lys Val
        115                 120                 125

Thr Thr Val Val Pro Met Asn Ala Leu Ser Thr Ser Tyr Pro Pro Ser
130                 135                 140

Asp Gly Ala Phe Gly Asp Ile Thr Ser Ile Met Thr Ser Ile Met
145                 150                 155                 160

Ala Ile Leu Val Arg Gln Asp Ser Pro Leu Leu Ile Asn Val Tyr Pro
                165                 170                 175

Tyr Phe Ala Tyr Ala Ser Asp Pro Thr His Ile Ser Leu Asn Tyr Ala
            180                 185                 190

Leu Phe Thr Ser Thr Ala Pro Val Val Asp Gln Gly Leu Glu Tyr
        195                 200                 205

Tyr Asn Leu Phe Asp Gly Met Val Asp Ala Phe Asn Ala Ala Leu Asp
    210                 215                 220

Lys Ile Gly Phe Gly
225

<210> SEQ ID NO 8
<211> LENGTH: 229
<212> TYPE: PRT
<213> ORGANISM: Gossypium hirsutum

<400> SEQUENCE: 8

```
Gly Arg Asp Ile Gly Val Cys Tyr Gly Leu Asn Gly Asn Asn Leu Pro
1               5                   10                  15

Ser Pro Gly Asp Val Ile Asn Leu Tyr Lys Thr Ser Gly Ile Asn Asn
            20                  25                  30

Ile Arg Leu Tyr Gln Pro Tyr Pro Glu Val Leu Glu Ala Ala Arg Gly
        35                  40                  45

Ser Gly Ile Ser Leu Ser Met Gly Pro Arg Asn Glu Asp Ile Gln Ser
    50                  55                  60

Leu Ala Lys Asp Gln Ser Ala Ala Asp Ala Trp Val Asn Thr Asn Ile
65                  70                  75                  80

Val Pro Tyr Lys Asp Asp Val Gln Phe Lys Leu Ile Thr Ile Gly Asn
                85                  90                  95

Glu Ala Ile Ser Gly Gln Ser Ser Ser Tyr Ile Pro Asp Ala Met Asn
            100                 105                 110

Asn Ile Met Asn Ser Leu Ala Leu Phe Gly Leu Gly Thr Thr Lys Val
        115                 120                 125

Thr Thr Val Val Pro Met Asn Ala Leu Ser Thr Ser Tyr Pro Pro Ser
    130                 135                 140

Asp Gly Ala Phe Gly Ser Asp Ile Thr Ser Ile Met Thr Ser Ile Met
145                 150                 155                 160

Ala Ile Leu Ala Val Gln Asp Ser Pro Leu Leu Ile Asn Val Tyr Pro
                165                 170                 175

Tyr Phe Ala Tyr Ala Ser Asp Pro Thr His Ile Ser Leu Asp Tyr Ala
            180                 185                 190

Leu Phe Thr Ser Thr Ala Pro Val Val Asp Gln Gly Leu Glu Tyr
        195                 200                 205

Tyr Asn Leu Phe Asp Gly Met Val Asp Ala Phe Asn Ala Ala Leu Asp
    210                 215                 220

Lys Ile Gly Phe Gly
225
```

<210> SEQ ID NO 9
<211> LENGTH: 6009
<212> TYPE: DNA
<213> ORGANISM: Gossypium hirsutum
<220> FEATURE:
<221> NAME/KEY: misc_feature
<222> LOCATION: (2278)..(2281)
<223> OTHER INFORMATION: TATA box
<220> FEATURE:
<221> NAME/KEY: misc_feature
<222> LOCATION: (2308)..(2308)
<223> OTHER INFORMATION: Transcription initiation site
<220> FEATURE:
<221> NAME/KEY: misc_feature
<222> LOCATION: (2308)..(2409)
<223> OTHER INFORMATION: 5' untranslated leader sequence
<220> FEATURE:
<221> NAME/KEY: misc_feature
<222> LOCATION: (2410)..(2412)
<223> OTHER INFORMATION: translation initiation codon (ATG)
<220> FEATURE:
<221> NAME/KEY: misc_feature
<222> LOCATION: (2410)..(2443)
<223> OTHER INFORMATION: coding sequence part I

```
<220> FEATURE:
<221> NAME/KEY: misc_feature
<222> LOCATION: (2444)..(2555)
<223> OTHER INFORMATION: intron sequence
<220> FEATURE:
<221> NAME/KEY: misc_feature
<222> LOCATION: (2556)..(3499)
<223> OTHER INFORMATION: coding sequence part II
<220> FEATURE:
<221> NAME/KEY: misc_feature
<222> LOCATION: (3497)..(3499)
<223> OTHER INFORMATION: translation stop codon
<220> FEATURE:
<221> NAME/KEY: misc_feature
<222> LOCATION: (3624)..(3624)
<223> OTHER INFORMATION: polyadenylation site

<400> SEQUENCE: 9
cgcggcatat aattttatgt gtgtaatttg ttgggttaat tacttaaaat agtatatttt      60
taattgctgt aattaatgta agataatttt tattatttga atcattgcac aaaattaaaa     120
tagaataatt tatttaacaa ttcaaatata ataataatcc aaattataat tatagtatt     180 ttacaatatt caatatacaa tatagttttta cttcatacaa ttaatataaa aaaatattat   240
tcaaaataat aactaataaa cataattacc atatattaat tattttgata tttcgaacat    300
aacgctaata aaaaatttcc taatcattat taaatcattt gtataaacta taagaaatt     360 gatatattgt aaattaaact ttattcattt ttttcttaa tactcaataa attaatcata    420
ataactcata ataatatat aattaaaata atcataacat ggtagattat ataaataggg     480
ggcgaatcta gggagctggc atgacccta aaatagaatt ttctattttg acctatcaaa     540
atttttaaaa ttttaaatta gtaaaggtaa atttgtactt tgacctctta aaatgataaa    600
attttacttt aatcctttaa aatttacatt tttactatca taaaaattac aatttgatt     660 tgcccctaaa atttttttct agcttagccc tgtatataaa tatattattt ataattttta   720
tatttaaaat ataagttttt taattataca aataattaaa atctgatatt taaaactaaa    780
gtaatttctt ttttctttt acttttttt aattgcaaca taatggttta aatatctata     840
taacgtatga agtaatttga tataaatttt atttaatttt attattatat aaattcattt    900
agtaaaaact tttaatagaa tcaaaatttt tatttgtaaa ttcgataact tttcttatca   960
agtatatttg tgagaaccaa atatttagta aaattaatat tcttatttat aaatatgata   1020
aatcttataa aaaatatttt aaaatgaaaa aaattgtaca aatattataa aaaaatattt   1080
aaaatgaaaa acattgtaca aaggctatat aagaagttca aaagtttctt cgaccatgta   1140
ctcttataga gattatagat agattataaa actatatgta gtttctctta actttttaaat   1200 aagaggataa atgtattta atgtactcaa acttatatat ttttatattg acaataatat    1260
caatatcaac ctaattaaga ttcattctaa cattaatgtt gaagatttt aataaaagaa     1320 aaggttaata aattaattag aacacaaaca aacacaaatt taagtggtat gtaaggtcct   1380
tgacccaaag gaaaaatttg ttacgtcgat taaattataa attaatttaa agtaaaatta   1440
cattttaacc taaaaaaaga gaaaagtata tctaatttct tcgaaaatgg aaagaaaatt   1500
ataaatttat ggcatttcta aaaaaattct gaattcgcta ctaaaagatg aaattataaa   1560
atccgaagca ttaccagaag atggatcacc aaatcacaaa caatcaatga aaagtaatga   1620
taattaattg aaagtgagca tttaattttg atagccatat acttcctgct gaatttatag   1680
gttctcatta atgcaattaa attatattcg acacctttg aatgaaataa aatgacacaa     1740
gaggaaagac ggttcatcta tttttctctt caatcgccca tcaaaatacc aaaaatgtaa   1800
```

```
ctacatgcaa aaaatcaaat atgaaaaata ttcatatttt gatattttaa tatattgtgt    1860
gttcaaaacg taaatgtatt gaaaaattat gatggtgttg ttgctgtatg tccataaaat    1920
tcaatgtact cacatttatc aaatgtatac tttgagagaa gttattttga taatactcaa    1980
gtttttttta tagatgggaa aattttttaa attattttt gattttgatg aaatgtatat     2040
ataaatttta attcgataca tataaatata tatgtaaatt ttaaatttaa atttaataat    2100
atacaattaa gaaataatt tataaatatt ttccgattaa aaataaatct ggaaagaaga     2160
aatgtcaaca cttttttcatt aaatacaatt aggatgggac acgatacctt catgcattga   2220
tatctcaggt ggtccaaaaa ctcggaatcc ttttttgaaaa aaaacttcca gagagagtat   2280
ataaatccag cagtaggcac aagaaacgag caccagttat tgactttcct ttgtaaaaaa   2340
aaaaagtgct gagatcaaga aatatagtga aatatgggtc caagattttc tgggttttta   2400
atctaagcaa tgctgttttt aactcaactc ctctctctaa caggtaaaac aaacttctct   2460
acagtgattt tacagtaaat atggctttga aaaatataca acaaaacatt tatcttcaat   2520
ccattttaat tactgatcta ctatatatgt tgcagatggc cgtgatattg gtgtttgcta   2580
tggtttgaac ggcaacaatc ttccatctcc aggagatgtt attaatcttt tcaaaactag   2640
tggcataaac aatatcaggc tctaccagcc ttaccctgaa gtgctcgaag cagcaagggg   2700
atcgggaata tccctctcga tgagtacgac aaacgaggac atacaaagcc tcgcaacgga   2760
tcaaagtgca gccgatgcat gggttaacac caacatcgtc ccttataagg aagatgttca   2820
attcaggttc atcatcattg ggaatgaagc cattccagga cagtcaagct cttacattcc   2880
tggtgccatg aacaacataa tgaactcgct ggcctcattt gggctaggca cgacgaaggt   2940
tacgaccgtg gtcccgatga atgccctaag tacctcgtac cctccttcag acggcgcttt   3000
tggaagcgat ataacatcga tcatgactag tatcatggcc attctggttc gacaggattc   3060 gccccctcctg atcaatgtgt accttatttt tgcctatgcc tcagacccca ctcatatttc   3120
cctcaactac gccttgttca cctcgaccgc accggtggtg gtcgaccaag gcttggaata   3180
ctacaacctc tttgacggca tggtcgatgc tttcaatgcc gccctagata agatcggctt   3240
cggccaaatt actctcattg tagccgaaac tggatggccg accgccggta acgagcctta   3300
cacgagtgtc gcgaacgctc aaacttataa caagaacttg ttgaatcatg tgacgcagaa   3360
agggactccg aaaagacctg aatatataat gccgacgttt ttcttcgaga tgttcaacga   3420
gaacttgaag caacccacag ttgagcagaa tttcggattc ttcttcccca atatgaaccc   3480
tgtttatcca ttttggtgaa cttgaaatgt tattgttggc tatttaaatc ttttgccaga   3540
gacgcttcat atagttcctg catattttga aagtggaaaa tcaatctaaa tataaataag   3600 tttttatttgt tgtttttttaa ttaaataaaa ttttaaatat tttaaaaaca tctttattgg   3660
taattaaata ttaaataaaa agtttaatat tcaaatttta tcaattcaaa aataaaataa    3720
aaatatatta aatttatttt tacgaataaa ttgattttct attaatgcag attttaaata    3780
atttgatata aattttcaat tcaacaatag taattttgat cacatcaaag gagaaaggga    3840
aagatttaac tttaattggt gacctaatat aacacgttga aaacggagtt cccaataagg    3900
caaaatgact tgtaatgacg aaagagatgt ccaagtgaaa tctgctttaa agtgaaagaa    3960
gcataaaagg ataactaaat aactcatgat ctaaattgaa gttctataaa atgcaacttt    4020
catctagaaa caaggtatgt cttaaatgat gttttatgaa tttgtcttaa ttgggtttta    4080
tgcaatgaat tcatggatag cacatctcta attatacgtt gctggtttat atgagagtgg    4140
tgcagaagtt aattgtgctt taaatacttg cttagtgttt atgaaatttg aaaagtgtta    4200
```

```
tatacttata ataaaaataa ttcgattcgg aatccaattc agggttcgac tcaatataat    4260
aaaattttac agatatcttg aagggggatct tcttcttctc tacttctcga gcagtgttat    4320
atatttacaa taaagataac tcaattcgag atccgaccta atataataaa attctacaga    4380
catatcaaag agggagatct tcttcttccc tacatcttga ccttcttgat caaaatgacc    4440
ttccttatat ttttacatac gttgattata tgaatcaaaa gaaagatacc aaaaagtttt    4500
taaaaataaa caacggggtt cttatgtaga gatgcttatg ggccgggccg gactcaacta    4560
aaaatttagg cacattcatt gggcccaggt cgggcctaac ccaaaaatgg gcctaaaatt    4620
ttgcccaagc ttgactcaaa taaaaatgct aaaattcggg cctgaccccg tattaatttt    4680
atattatttt ataactttt taaatatata taatatataa aaaatactaa aaaaattaaa    4740
ataaatattt cccaactaaa ctaaaattat taagaaaaat aattcatatt agcgtataaa    4800
ttggaaattg accaaaatta aaattattgt atagttaatc tatattaaaa ggacatgtaa    4860
ttaaaaacca ttaaaactat tatacaataa attaaatctt cattgtatac atagaaaggc    4920
attaataatt aaaaaactat attaagatat aaactaaatt caaaattatt aaaaacaaga    4980
actaaataaa aaagcaattg aaaattacga attaatgtta aaatcaaatg ttaaaatcaa    5040
gggacttaaa taaaaatatc ccaaaataca aaacattagc ttcctttccc atccacgtga    5100
atgcaaagtt tacatggtgt ttcctagtgt ttgtgcgact ccaaccttt atttacctct    5160 ttttttcttt atttgaacaa ttatttgata atgattagaa ttttgggatt gttgctcatc    5220
gtacgtgcaa cacttaaaat cactatgatt tttcataatt tatataacct atatcgtttt    5280
ggaaattaat tttatttttt atattatttt aataaaaata ccatctacct tttttaattt    5340 atgatcccctt tcatatttaa aaattcaaat tgacaattgt ctaactaaac accgtcacac    5400
tccaataaga ttgtaatttc ctccatcttg atattacact caaaagcatg ttgccaacaa    5460
acaaatcaac tagccttttt ctaccactat tcatcatctt cttaagagtg tgtttatgtc    5520
atgtgccgag attttaggta tggtcacgtt gtggctttaa actcaaatct attgcccatg    5580
agtctaagtt agcctccgat cctcactaaa gagaggcttg gcacacttta cctagccaag    5640
tacacaagga atagagctat tagaaagcat taaagagtta ggagaatgtg gaagtgtttt    5700
tattactcaa agctaacttg gatacaaata aaggagggag cctctccttt aggcaagctt    5760
cttttgatct gatggttaca attaatctcg aataggaggg gtcaaacttc tcactcagtt    5820
tcatattatc tcttggtgct tggttggcct ccgccttgag acaactttag ataacaccta    5880
gtcttaacac ttttagcttc acattgtacg catccttcat tactcaaatg ccacaaagcc    5940
tccttactta aggctcttgg tcgctcccac taccttcggc tttagactca tctaagatct    6000
tcccaatcg                                                              6009
```

<210> SEQ ID NO 10
<211> LENGTH: 6877
<212> TYPE: DNA
<213> ORGANISM: Gossypium hirsutum
<220> FEATURE:
<221> NAME/KEY: misc_feature
<222> LOCATION: (3242)..(3245)
<223> OTHER INFORMATION: TATA box
<220> FEATURE:
<221> NAME/KEY: misc_feature
<222> LOCATION: (3270)..(3270)
<223> OTHER INFORMATION: transctiption initiation site
<220> FEATURE:
<221> NAME/KEY: misc_feature
<222> LOCATION: (3270)..(3372)

<223> OTHER INFORMATION: 5' untranslated leader sequence
<220> FEATURE:
<221> NAME/KEY: misc_feature
<222> LOCATION: (3373)..(3375)
<223> OTHER INFORMATION: Translation start codon (ATG)
<220> FEATURE:
<221> NAME/KEY: misc_feature
<222> LOCATION: (3373)..(3406)
<223> OTHER INFORMATION: coding sequence part I
<220> FEATURE:
<221> NAME/KEY: misc_feature
<222> LOCATION: (3407)..(3500)
<223> OTHER INFORMATION: intron sequence
<220> FEATURE:
<221> NAME/KEY: misc_feature
<222> LOCATION: (3501)..(4444)
<223> OTHER INFORMATION: coding sequence part II
<220> FEATURE:
<221> NAME/KEY: misc_feature
<222> LOCATION: (4442)..(4444)
<223> OTHER INFORMATION: stop codon
<220> FEATURE:
<221> NAME/KEY: misc_feature
<222> LOCATION: (4566)..(4566)
<223> OTHER INFORMATION: polyadenylation site

<400> SEQUENCE: 10

```
ttcaaactta ctcgcttgca caaaaataat tttataaaag tatttaaaat ataaatttt      60
tatgttgata atatttttat atacatttta tattttaaga ataataatt ttttaggaat    120
tagaaaaaaa atgtagaata atatcattga tattttaatt tttcaaaaaa ttaaaaataa    180
gttcacgtag tctaatttta tctattttaa tttttatact ttcaaattga gataaatatc    240
aaagaacttt tggttcaata tgcaatttga tacttaaatt ttaatttgat gtaattatta    300
catgaaactt ggcttgtggt ttatacgtat acatgaaatt tttattttga ttcaattgta    360
cgcatttaaa gaaatgaaaa tggttctaat tcaataatat tattagtgat ttgtgaaatt    420
taaaactttt atgcattaaa ccacacaaaa tcagagttta tgtatgatat tgcacattgg    480
actatagttc atgcatattt tttatatttt atccatgtca aattttgaaa tttcattctt    540
aacttatatg atagcagtta aatttgttaa gtcaaactct agtattagtt atatactata    600
cataacttgt agagtttagt ttaagttcac taatttgatt atttttttatc tgtttatttt    660
ttcaatttca agatttaagt tttaagctta acttaaacaa tagtcattaa atttattaac    720
taaaatgtcc tggggttttt tgtaagtatt ataaatatgtt tgccacgtga gattttggta    780
aaagtagagt ttaacttaac aaatttaatg gctactactt agtaaggatt agaatttcaa    840
aattaaaaaa aaaattatag aggctaaaga tgatcaaatt agaggtttaa attaagtcaa    900
attaaaatag ttctggatat taactattta aattaattaa tgtcattata aaattagagg    960
tctaaattat gtaaaattaa aatataaaaa ctaaatctcg aatgtgagta tagtataagg   1020
atcaaaagtg attttggtca ttttctttta tttacaaata ttcttagaga tgctctttta   1080
tatataatgg tttctaatgt gatatgcgcg gcataatt ttatgtgttt aatttatttt    1140
attaattatt taaataatat attttttaatt actataatta atgtaaaata ttttttatta   1200
tttgaatcac tgcacaaaat taaaatatac taacttaatt aacaattcaa atataataat   1260
aatctaaatt ataattaaag cattttttaca atattcagta tataatatag ttttacttta   1320
tataattaat acaaagaaat attattcaaa ataatactaa atcaacataa ttactatata   1380
tcaattattt tgatatttcg aacataatgc taataaaaaa tttcctaatc attattaaat   1440
catttgtata aactataaag aaattgatat attgtaaatt aaactttttaa ctattcaatt   1500
ttttcttaat agtcaataaa ttaatcataa taattcataa ttaatatata attaacataa   1560
```

```
ccataacata gaattttta ttttggccca ttaaaattt taaaatttta aattagtaaa      1620
ggaaaaatta cactttgacc ccttaaaaat gataaaattt tattttaatc ctttaaaatt    1680 gacatttta ctattgtaaa aattacaatt taattttgcc ccctaaaaa atttttctag      1740 cttcgcccett gtgtataaat atattaatta caattttat atttgaatta tataaataat    1800 taaatttga tatttaaaac taaagtaatc tctttttttt ttactttttt ttaattgaaa     1860
cataatggtt taaatatcta tattacgtat gaagtaattt aatataaatt ttattttaat    1920
ttattattat ataaattcat ttagtaaaaa cttttaatag aatcaaaatt tttatttgta    1980
aattcgataa cttttcttat caagtaaatt tgttgaatta aatatttagt aaaattaata    2040
tttttattta taaatatgat aaatcttata aaaataaaa aaatatttaa aatgaaaaac     2100
attgtacaaa ggctatataa gaagttcaaa agtttcttcg accctgtact ctaatagaga    2160
ttatagatag attatagaac tattcatagt ttctcttaac ctttaaataa gaattttagt    2220
gtactcaaac ttacatattt ttatattgat aataatgtca ataccagccg agttaagatt    2280
cactcgacat taatgttgaa aatttttaat aaaagaaaat gttgataagt taattagaac    2340
acaagcaagc acaaatttaa gtggtaagta aggtccttga ccctaatgga aaaattgtta    2400
tgttgattaa attataaatt aatttaaggt aaaattatat tttgacctaa aaaaatgaaa    2460
aaaatatatc tagtttcttc gaaaatgaaa agaaaataat aaattgatac attataaaat    2520
ttatggcatt tctaaaaaa ttctgaattt gatgaaatta taataaaaaa aaagtttaaa     2580
aacatataga tttcaagaat agtgggaaaa ttatatttga acaacactga agaaatccaa    2640
agcattagca gaaaatggat caccaaatca caaacaatca gtgaaaagta atgataatta    2700
attgaaagtg agcatttaaa tttgatagcc atatacttcc tgctgaattt ataggttctc    2760
attaatgcaa ttaaattata tttgtcactt tttgaatgaa ataaatgaca cagttcatct    2820 atttttttc tttcaatcgc ccatcaaaat accgaaaatg taactacatt aaaaaagatc     2880
gaaaaatatt catattttga tattttaata gattgtgtgt tcaaggcgta atgtactaaa    2940
aaattatgat ggtgttgtcg ctgtatgtcc ataaaattca atgtattcgc atgtatcaaa    3000
tgtaaatttt gacacaagtt attctaataa taatcaagtt attttttatac atgagataca   3060 tctcaaaatt attttatat atccgaaaaa tcataacgta cgatcaaact agaaagagga     3120
agtgtcaaaa cctattcatt atatgcaaat atgatgggac acgataccct catgcattga    3180
tatctcatat tgtccaaaaa ctcagaatcc ttttgaaaa aaaaaaattc cagagagagt     3240
gtataaatcc agcagtgtgc acaagaaacg agcaccagtt attgacattc ctttgtaaaa    3300
aaaaaaagaa gctgagatca agaaatatag tgaaatatgg gtccaacatt ttctgggttt    3360
ttaatctcag caatggtgtt tttaactcaa ctcctctctc taacaggtaa aacaaacttc    3420
tctacagtga ttttacggta agtatggctt tgaaaaatat acaacaaaac atttatactg    3480
atctaccata tatgttgcag atggccgtga tattggtgtt tgctatggtt tgaacggcaa    3540
caatcttcca tctccaggag atgttattaa tctttacaaa actagtggca taaacaatat    3600
caggctctac cagccttacc ctgaagtgct cgaagcagca aggggatcgg gaatatccct    3660
ctcgatgggt ccgagaaacg aggacataca aagcctcgca aaagatcaaa gtgcagccga    3720
tgcatgggtt aacaccaaca tcgtccctta taaggacgat gttcagttca agttgatcac    3780
tattgggaat gaagccattt caggacaatc aagctcttac attcctgatg ccatgaacaa    3840
cataatgaac tcgctcgcct tatttgggtt aggcacgacg aaggttacga ccgtggtccc    3900
```

```
gatgaatgcc ctaagtacct cgtaccctcc ttcagacggc gcttttggaa gcgatataac    3960
atcgatcatg actagtatca tggccattct ggctgtacag gattcgcccc tcctgatcaa    4020
tgtgtaccct tattttgcct atgcctcaga ccccactcat atttccctcg attacgcctt    4080
gttcacctcg accgcaccgg tggtggtcga ccaaggcttg gaatactaca acctctttga    4140
cggcatggtc gatgctttca atgccgccct agataagatc ggcttcggcc aaattactct    4200
cattgtagcc gaaactggat ggccgaccgc cggtaacgag ccttacacga gtgtcgcgaa    4260
cgctcaaact tataacaaga acttgttaaa tcatgtgacg cagaagggga ctccgaaaag    4320
acctgaatat ataatgccga cgttttttctt cgagatgttc aacgaggatt tgaagcaacc    4380
cacagttgag cagaatttcg gattcttctt ccccaatatg aaccctgttt atccattttg    4440
gtgaagttga atgttgttg gctatttaaa tcttttgcca gagacgcttc atatagtttc    4500
tgcatatttt gaaagtggaa atcaatcta aatattaata agttttatgt gttgtttttt    4560
aattaaataa aattttaaat attttaaaaa tatcttatt ggtaattaaa tattaaataa    4620
aaagtttaat attcaaattt tatcaattca aaaataaaat aaaaatatat taaatttatt    4680
tttacgaata aattgatttt ctattaatac agattttgaa taatttgata taaattttaa    4740
attcaacaat agtaattttg atcacatcaa aggagaaagg gaaagattta actttaattg    4800
gtgacctaat ataacacgtt gaaaacggag ctcccaggaa ggcaaaatga cttgtaatga    4860
cgaaagagat gtccaagtag aatctgcatt aaagtgaaaa aagcataaaa ggataagtaa    4920
actcatgatc tgacataaat tgaagttcta taaaatgcaa ctttcatcta gaaacaaggt    4980
atgtcttaaa tgatgtttta tgaatttgtc ttaactgggt tttatgcaat gaattcatgg    5040
atagcacctc actaattata cgttgctggt ttatatgaga gtggtgcaga agttaattgt    5100
gctttaaata cttgcttagt gttcaagaaa tttgaaaagt attatatatt tataataaaa    5160
ataattcaga tccgactcaa tctagtaaaa ttttacaaac attctaaagg ggatcttctt    5220
ttttctctac ttattgatca gtgttatata cttataataa agacaacctg atttgagatc    5280
cggcctaata taataaaatt ctacagacat ctcaagggag agatcttctt cttccctaca    5340
tcttgacctt tttgatcaaa atttcctccc ctctatttcc acattggttg atcatatgaa    5400
tcaacagaaa ggtaccaaaa agttttttaaa aataaacaaa ggggttctta tgaaattcat    5460
atgatatatt gggtctaatt attagaatca atttttaagtt taaacaaatt taaaattcaa    5520
aactcaattc cattttttgtt tgaacggaaa gttactaatt gttaagaaaa ataattcata    5580
ttagcgtata aattggaaat tgaccaaaac taaaattatt gtatagttaa tctatattaa    5640
aaggacatgt aattaaaaac cattaaaact attatagaat aaattaaatc ttcattctat    5700
acatacaaag tcattaataa ttaaaaaact atattaagat ataaactata ttcaaaaaat    5760
attaaaaaca ataactaaat aaaaaaaaca attgaaaatt acgaattaat gttaaaatca    5820
agggacttaa ataaaaatat cccaaaatac aaaacattag cttccttttcc catccacgtg    5880 attgcaaagt ttacatggtg tttcctagtg cttgtgcgac tccaaccttt tatttacttt    5940
tttcttttct ttatttgaac aattatttga taatgattag aattttggga ttgttgctca    6000
tcgtacgtgc aacacttaaa atcactatga tttttcataa tttatataac ctatatcgtt    6060
ttggaaatta atgttattat ttatattgtt ttaataaaaa taccatctac ctctttaat    6120 ttatgatcca tttcttattt gaaaattcaa attgacagtt gtctaactaa acaccatcgc    6180
actccaataa aattgtaatt ttttctatcg tgaaatagtac actcaaaagt atgttgttaa    6240
caaacaaatc aattagccctt tttctacctc tattcatcat cttcttaata gcgtgtttat    6300
```

```
gtcacgtgtt gagattttag ttccggtcac gtgtggcctt aaacccgaat ttcttacgca   6360
tgagtctaag ttagcctctg atcctcgcta tggagatgct tggcacagtt tacctaggta   6420
agtaaacaag aatagagct attagaaagc atcagagagt taggagaatg tggaagtgtt   6480
tctattactc aaagctaact tggatacaaa taaaagaggg agcctctcct ttaggcaagc   6540
ctattttgat ctgacggttg caattaatct cgaataggag gggtcgaact tctcactcag   6600
tttcacatta tctcttggtg cttagttggc ctccgccttg agacacattc aaataacacc   6660
tagtcttaac acttttggct tcttattgtg cgtatccttc attactcaaa tgccacaaag   6720
cctcattact taagactctc ggtcgctccc actaccttcg actttagact catctaagat   6780
cttcccaatc gtagacaact tggccttggt ggggaaatct tgcaccctac ggggccttac   6840
ataagaagca attaaatggc tttctctcac ccacctt                             6877
```

<210> SEQ ID NO 11
<211> LENGTH: 325
<212> TYPE: PRT
<213> ORGANISM: Gossypium hirsutum

<400> SEQUENCE: 11

```
Met Leu Phe Leu Thr Gln Leu Leu Ser Leu Thr Asp Gly Arg Asp Ile
1               5                   10                  15

Gly Val Cys Tyr Gly Leu Asn Gly Asn Asn Leu Pro Ser Pro Gly Asp
            20                  25                  30

Val Ile Asn Leu Phe Lys Thr Ser Gly Ile Asn Asn Ile Arg Leu Tyr
        35                  40                  45

Gln Pro Tyr Pro Glu Val Leu Glu Ala Ala Arg Gly Ser Gly Ile Ser
    50                  55                  60

Leu Ser Met Ser Thr Thr Asn Glu Asp Ile Gln Ser Leu Ala Thr Asp
65                  70                  75                  80

Gln Ser Ala Ala Asp Ala Trp Val Asn Thr Asn Ile Val Pro Tyr Lys
                85                  90                  95

Glu Asp Val Gln Phe Arg Phe Ile Ile Ile Gly Asn Glu Ala Ile Pro
            100                 105                 110

Gly Gln Ser Ser Ser Tyr Ile Pro Gly Ala Met Asn Asn Ile Met Asn
        115                 120                 125

Ser Leu Ala Ser Phe Gly Leu Gly Thr Thr Lys Val Thr Thr Val Val
    130                 135                 140

Pro Met Asn Ala Leu Ser Thr Ser Tyr Pro Pro Ser Asp Gly Ala Phe
145                 150                 155                 160

Gly Ser Asp Ile Thr Ser Ile Met Thr Ser Ile Met Ala Ile Leu Val
                165                 170                 175

Arg Gln Asp Ser Pro Leu Leu Ile Asn Val Tyr Pro Tyr Phe Ala Tyr
            180                 185                 190

Ala Ser Asp Pro Thr His Ile Ser Leu Asn Tyr Ala Leu Phe Thr Ser
        195                 200                 205

Thr Ala Pro Val Val Asp Gln Gly Leu Glu Tyr Tyr Asn Leu Phe
    210                 215                 220

Asp Gly Met Val Asp Ala Phe Asn Ala Ala Leu Asp Lys Ile Gly Phe
225                 230                 235                 240

Gly Gln Ile Thr Leu Ile Val Ala Glu Thr Gly Trp Pro Thr Ala Gly
                245                 250                 255

Asn Glu Pro Tyr Thr Ser Val Ala Asn Ala Gln Thr Tyr Asn Lys Asn
            260                 265                 270
```

```
Leu Leu Asn His Val Thr Gln Lys Gly Thr Pro Lys Arg Pro Glu Tyr
            275                 280                 285

Ile Met Pro Thr Phe Phe Glu Met Phe Asn Glu Asn Leu Lys Gln
290                 295                 300

Pro Thr Val Glu Gln Asn Phe Gly Phe Phe Pro Asn Met Asn Pro
305                 310                 315                 320

Val Tyr Pro Phe Trp
            325

<210> SEQ ID NO 12
<211> LENGTH: 325
<212> TYPE: PRT
<213> ORGANISM: Gossypium hirsutum

<400> SEQUENCE: 12

Met Val Phe Leu Thr Gln Leu Leu Ser Leu Thr Asp Gly Arg Asp Ile
1               5                   10                  15

Gly Val Cys Tyr Gly Leu Asn Gly Asn Leu Pro Ser Pro Gly Asp
            20                  25                  30

Val Ile Asn Leu Tyr Lys Thr Ser Gly Ile Asn Asn Ile Arg Leu Tyr
            35                  40                  45

Gln Pro Tyr Pro Glu Val Leu Glu Ala Ala Arg Gly Ser Gly Ile Ser
50                  55                  60

Leu Ser Met Gly Pro Arg Asn Glu Asp Ile Gln Ser Leu Ala Lys Asp
65                  70                  75                  80

Gln Ser Ala Ala Asp Ala Trp Val Asn Thr Asn Ile Val Pro Tyr Lys
            85                  90                  95

Asp Asp Val Gln Phe Lys Leu Ile Thr Ile Gly Asn Glu Ala Ile Ser
                100                 105                 110

Gly Gln Ser Ser Ser Tyr Ile Pro Asp Ala Met Asn Asn Ile Met Asn
            115                 120                 125

Ser Leu Ala Leu Phe Gly Leu Gly Thr Thr Lys Val Thr Thr Val Val
            130                 135                 140

Pro Met Asn Ala Leu Ser Thr Ser Tyr Pro Pro Ser Asp Gly Ala Phe
145                 150                 155                 160

Gly Ser Asp Ile Thr Ser Ile Met Thr Ser Ile Met Ala Ile Leu Ala
                165                 170                 175

Val Gln Asp Ser Pro Leu Leu Ile Asn Val Tyr Pro Tyr Phe Ala Tyr
            180                 185                 190

Ala Ser Asp Pro Thr His Ile Ser Leu Asp Tyr Ala Leu Phe Thr Ser
            195                 200                 205

Thr Ala Pro Val Val Asp Gln Gly Leu Glu Tyr Tyr Asn Leu Phe
210                 215                 220

Asp Gly Met Val Asp Ala Phe Asn Ala Ala Leu Asp Lys Ile Gly Phe
225                 230                 235                 240

Gly Gln Ile Thr Leu Ile Val Ala Glu Thr Gly Trp Pro Thr Ala Gly
            245                 250                 255

Asn Glu Pro Tyr Thr Ser Val Ala Asn Ala Gln Thr Tyr Asn Lys Asn
            260                 265                 270

Leu Leu Asn His Val Thr Gln Lys Gly Thr Pro Lys Arg Pro Glu Tyr
            275                 280                 285

Ile Met Pro Thr Phe Phe Glu Met Phe Asn Glu Asp Leu Lys Gln
290                 295                 300

Pro Thr Val Glu Gln Asn Phe Gly Phe Phe Pro Asn Met Asn Pro
```

Val Tyr Pro Phe Trp
               325

<210> SEQ ID NO 13
<211> LENGTH: 134
<212> TYPE: DNA
<213> ORGANISM: Artificial
<220> FEATURE:
<223> OTHER INFORMATION: pre-miRA1
<220> FEATURE:
<221> NAME/KEY: misc_feature
<222> LOCATION: (17)..(36)
<223> OTHER INFORMATION: miRNA strand I
<220> FEATURE:
<221> NAME/KEY: misc_feature
<222> LOCATION: (87)..(107)
<223> OTHER INFORMATION: miRNA strand II

<400> SEQUENCE: 13
tctagggtaa gggaggtcct gtcgaaccag aatggcacag ggtactttct tgcatgcttg      60
agcctttcat gcttgaagct ctgcgccatt ctcgttcaga caggatccac tttctctct     120 ctctctcact cact                                                      134

<210> SEQ ID NO 14
<211> LENGTH: 146
<212> TYPE: DNA
<213> ORGANISM: Artificial
<220> FEATURE:
<223> OTHER INFORMATION: premiRA1 with cloning sites

<400> SEQUENCE: 14
ccatggtcta gggtaaggga ggtcctgtcg aaccagaatg cacagggta ctttcttgca      60 tgcttgagcc tttcatgctt gaagctctgc gccattctcg ttcagacagg atccactttt    120
ctctctctct ctcactcact gctagc                                         146

<210> SEQ ID NO 15
<211> LENGTH: 134
<212> TYPE: DNA
<213> ORGANISM: Artificial
<220> FEATURE:
<223> OTHER INFORMATION: pre-miRD1
<220> FEATURE:
<221> NAME/KEY: misc_feature
<222> LOCATION: (17)..(36)
<223> OTHER INFORMATION: miRNA strand I
<220> FEATURE:
<221> NAME/KEY: misc_feature
<222> LOCATION: (87)..(107)
<223> OTHER INFORMATION: miRNA strand II

<400> SEQUENCE: 15
tctagggtaa gggaggatcc tgtacagcca gaatggacag ggtactttct tgcatgcttg      60
agcctttcat gcttgaagct ctgcccattc tgcctgtaac aggattccac tttctctct     120 ctctctcact cact                                                      134

<210> SEQ ID NO 16
<211> LENGTH: 146
<212> TYPE: DNA
<213> ORGANISM: Artificial
<220> FEATURE:
<223> OTHER INFORMATION: pre-miRD1 with cloning sites

<400> SEQUENCE: 16

```
ccatggtcta gggtaaggga ggatcctgta cagccagaat ggacagggta ctttcttgca    60
tgcttgagcc tttcatgctt gaagctctgc ccattctgcc tgtaacagga ttccactttt   120
ctctctctct ctcactcact gctagc                                        146

<210> SEQ ID NO 17
<211> LENGTH: 134
<212> TYPE: DNA
<213> ORGANISM: Artificial
<220> FEATURE:
<223> OTHER INFORMATION: pre-miRA2
<220> FEATURE:
<221> NAME/KEY: misc_feature
<222> LOCATION: (17)..(36)
<223> OTHER INFORMATION: microRNA strand I
<220> FEATURE:
<221> NAME/KEY: misc_feature
<222> LOCATION: (87)..(107)
<223> OTHER INFORMATION: microRNA strand II

<400> SEQUENCE: 17
tctagggtaa gggaggttcc caatgatgat gaacctacag ggtactttct tgcatgcttg    60
agcctttcat gcttgaagct ctgcaggttc atcatcaatt gggaatccac ttttctctct   120
ctctctcact cact                                                     134

<210> SEQ ID NO 18
<211> LENGTH: 134
<212> TYPE: DNA
<213> ORGANISM: Artificial
<220> FEATURE:
<223> OTHER INFORMATION: pre-miRA2aa
<220> FEATURE:
<221> NAME/KEY: misc_feature
<222> LOCATION: (17)..(36)
<223> OTHER INFORMATION: microRNA strand I
<220> FEATURE:
<221> NAME/KEY: misc_feature
<222> LOCATION: (87)..(107)
<223> OTHER INFORMATION: microRNA strand II

<400> SEQUENCE: 18
tctagggtaa gggaggttcc caatgatgat gaacctacag ggtactttct tgcatgcttg    60
agcctttcat gcttgaagct ctgcaggttc ataatcactt gggaatccac ttttctctct   120
ctctctcact cact                                                     134

<210> SEQ ID NO 19
<211> LENGTH: 146
<212> TYPE: DNA
<213> ORGANISM: Artificial
<220> FEATURE:
<223> OTHER INFORMATION: pre-miRA2aa with cloning sites

<400> SEQUENCE: 19
ccatggtcta gggtaaggga ggttcccaat gatgatgaac ctacagggta ctttcttgca    60
tgcttgagcc tttcatgctt gaagctctgc aggttcataa tcacttggga atccactttt   120
ctctctctct ctcactcact gctagc                                        146

<210> SEQ ID NO 20
<211> LENGTH: 134
<212> TYPE: DNA
<213> ORGANISM: Artificial
<220> FEATURE:
<223> OTHER INFORMATION: pre-miRD2
<220> FEATURE:
<221> NAME/KEY: misc_feature
```

```
<222> LOCATION: (17)..(36)
<223> OTHER INFORMATION: microRNA strand I
<220> FEATURE:
<221> NAME/KEY: misc_feature
<222> LOCATION: (87)..(107)
<223> OTHER INFORMATION: microRNA strand II

<400> SEQUENCE: 20
tctagggtaa gggaggattc ccaatagtga tcaactacag ggtactttct tgcatgcttg      60
agcctttcat gcttgaagct ctgcagttga tccctatatg ggaattccac ttttctctct    120
ctctctcact cact                                                      134

<210> SEQ ID NO 21
<211> LENGTH: 146
<212> TYPE: DNA
<213> ORGANISM: Artificial
<220> FEATURE:
<223> OTHER INFORMATION: pre-miRD2 with cloning sites

<400> SEQUENCE: 21
ccatggtcta gggtaaggga ggattcccaa tagtgatcaa ctacagggta ctttcttgca     60
tgcttgagcc tttcatgctt gaagctctgc agttgatccc tatatgggaa ttccactttt   120
ctctctctct ctcactcact gctagc                                        146
```